(12) United States Patent
Li et al.

(10) Patent No.: US 10,495,579 B2
(45) Date of Patent: Dec. 3, 2019

(54) SYSTEM AND METHOD FOR COMPENSATION OF ILLUMINATION BEAM MISALIGNMENT

(71) Applicant: KLA-Tencor Corporation, Milpitas, CA (US)

(72) Inventors: Frank Li, Danville, CA (US); Zhiwei Xu, Sunnyvale, CA (US); Timothy Swisher, Hayward, CA (US); Kwan Auyeung, Fremont, CA (US); Yury Yuditsky, Mountain View, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 133 days.

(21) Appl. No.: 15/477,885

(22) Filed: Apr. 3, 2017

(65) Prior Publication Data
US 2017/0336329 A1 Nov. 23, 2017

Related U.S. Application Data

(60) Provisional application No. 62/330,756, filed on May 2, 2016.

(51) Int. Cl.
*G01N 21/88* (2006.01)
*G01N 21/95* (2006.01)
(Continued)

(52) U.S. Cl.
CPC ..... *G01N 21/8806* (2013.01); *G01N 21/9501* (2013.01); *G01N 21/956* (2013.01); *G02B 26/108* (2013.01)

(58) Field of Classification Search
CPC ....... G01N 21/8851; G01N 2021/8887; G01N 21/8806; G01N 21/95; G06T 7/0004
(Continued)

(56) References Cited

U.S. PATENT DOCUMENTS

| 4,696,047 A | 9/1987 | Christian et al. |
| 6,831,736 B2 | 12/2004 | Elichai et al. |

(Continued)

FOREIGN PATENT DOCUMENTS

| JP | 2001334376 A | 12/2001 |
| JP | 2003179142 A | 6/2003 |

(Continued)

OTHER PUBLICATIONS

ACS Motion Control, "Dual Axis EtherCAT NanoPWM Drive Module", Aug. 2015, 2 pages, Ver 3.0, www.acsmotioncontrol.com.

*Primary Examiner* — Jade R Chwasz
(74) *Attorney, Agent, or Firm* — Suiter Swantz pc llo

(57) ABSTRACT

A system includes a beam steering assembly configured to adjust an incident beam to form a corrected beam; a beam monitoring assembly configured to generate monitoring data for the corrected beam including one or more offset parameters of the corrected beam; and a controller configured to store one or more zero parameters of the corrected beam, calculate at least one difference between the one or more zero parameters and the one or more offset parameters of the corrected beam, determine one or more beam position adjustments of the incident beam based on the at least one difference between the one or more zero parameters and the one or more offset parameters of the corrected beam, and direct the beam steering assembly via one or more motor drivers to actuate one or more motors to adjust the incident beam to form the corrected beam.

44 Claims, 19 Drawing Sheets

(51) Int. Cl.
*G01N 21/956* (2006.01)
*G02B 26/10* (2006.01)

(58) Field of Classification Search
USPC .......................................................... 359/17
See application file for complete search history.

(56) References Cited

U.S. PATENT DOCUMENTS

| | | |
|---|---|---|
| 7,149,234 B2 | 12/2006 | Das et al. |
| 7,307,711 B2 * | 12/2007 | Lizotte ................. G01B 11/272 356/151 |
| 8,379,204 B1 | 2/2013 | Cordingley et al. |
| 8,885,146 B2 | 11/2014 | DeVoe et al. |
| 2004/0109487 A1 | 6/2004 | Zhang |
| 2006/0202115 A1 * | 9/2006 | Lizotte ................... B23K 26/04 250/234 |
| 2013/0151185 A1 | 6/2013 | Yagoshi |
| 2015/0170357 A1 | 6/2015 | Cao et al. |

FOREIGN PATENT DOCUMENTS

| | | |
|---|---|---|
| KR | 20080014385 A | 2/2008 |
| KR | 20110050821 A | 5/2011 |

\* cited by examiner

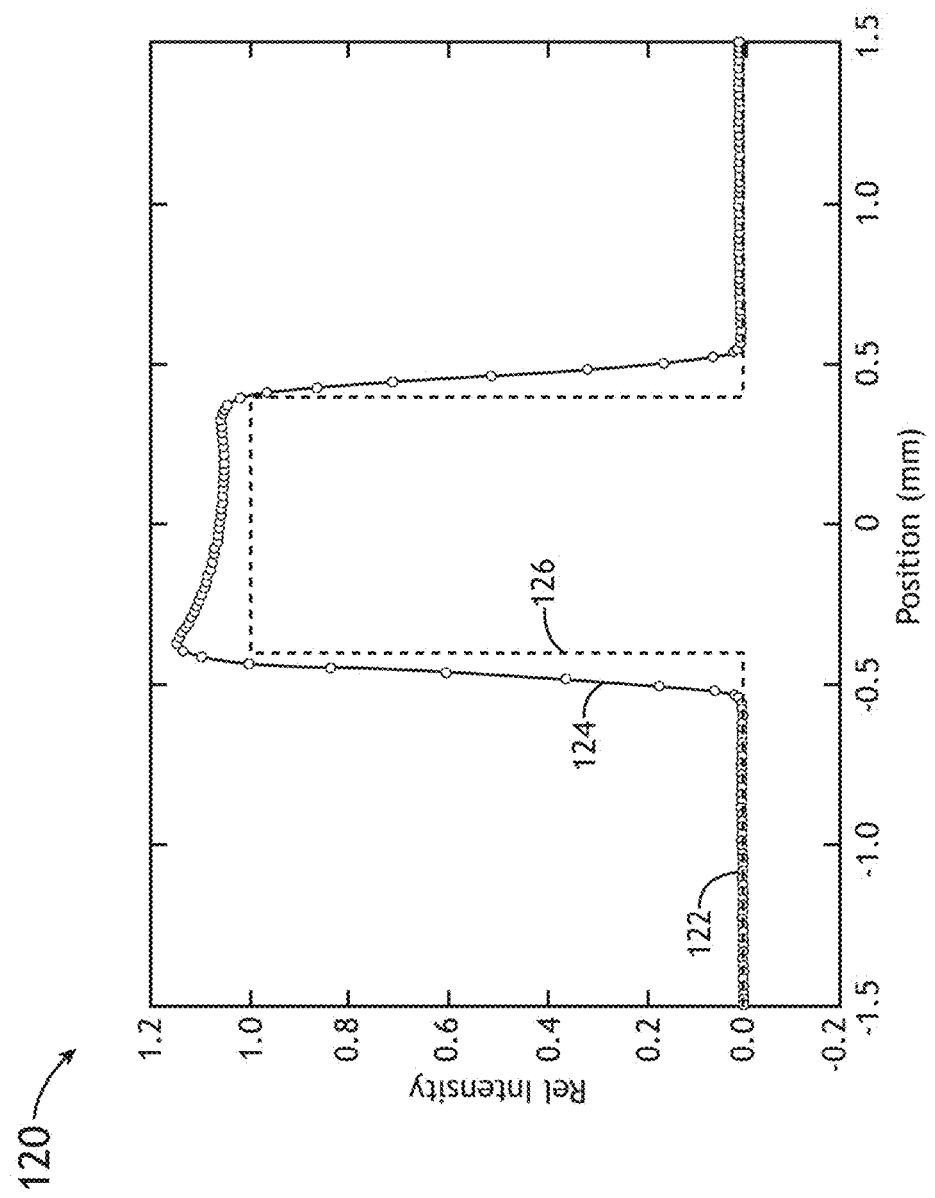

SYSTEM AND METHOD FOR COMPENSATION OF ILLUMINATION BEAM MISALIGNMENT

CROSS-REFERENCE TO RELATED APPLICATIONS

The present application claims priority under 35 U.S.C. § 119(e) to U.S. Provisional Patent Application Ser. No. 62/330,756, filed May 2, 2016, entitled METHOD AND SYSTEM FOR ACTIVE COMPENSATION OF ILLUMINATION LASER BEAM JITTER FOR WAFER INSPECTION SYSTEM, naming Frank Li, Steve Xu, Tim Swisher, Kwan Auyeung, and Yury Yuditsky as inventors, which is incorporated herein by reference in the entirety.

TECHNICAL FIELD

The present invention generally relates to wafer inspection and review, and, in particular, to adjusting an illumination beam in an inspection system to compensate for misalignment.

BACKGROUND

Fabricating semiconductor devices such as logic and memory devices typically includes processing a substrate such as a semiconductor wafer using a large number of semiconductor fabrication processes to form various features and multiple levels of the semiconductor devices. Multiple semiconductor devices may be fabricated in an arrangement on a single semiconductor wafer and then separated into individual semiconductor devices.

Semiconductor devices may develop defects during the fabrication processes. As the demand for integrated circuits having ever-smaller device features continues to increase, the need for improved inspection systems of these ever-shrinking devices continues to grow. Compensating for misalignment of an illumination beam in these improved inspection systems becomes more and more critical, as even minute system jitter may directly impact capture rate of the ever-smaller devices.

System jitter may originate from multiple sources, resulting in a jitter frequency distribution ranging from 0.1 Hz to 100 Hz. One system jitter source is "air wiggle", or turbulent air flow along the illumination beam path caused by purge air creating zones of pressure change and changing the refractive index of the air, which affects the pointing and translation components of a position of the illumination beam in a frequency range of 5 Hz to 100 Hz. Another system jitter source is the illumination light source, which will have intrinsic instabilities ranging in frequency from 0.5 to 10 Hz. A third source of system jitter is the mechanical vibration of inspection system components such as optic mounts and mechanical contacts, potentially excited by various external forces, which affect the pointing and translation components of the position of the illumination beam in a frequency range of 0.1 Hz to 100 Hz.

These system jitter sources are often too difficult to effectively remove from the inspection system, meaning the illumination beam will remain misaligned if not compensated for within the improved inspection systems.

As such, it would be desirable to provide a system and method for curing the shortcomings of previous approaches such as those identified above.

SUMMARY

A system is disclosed, in accordance with one or more embodiments of the present disclosure. In one illustrative embodiment, the system includes a beam steering assembly configured to adjust an incident beam to form a corrected beam. In another illustrative embodiment, the system includes a beam monitoring assembly optically coupled to the beam steering assembly. In another illustrative embodiment, the beam monitoring assembly is configured to generate monitoring data for the corrected beam. In another illustrative embodiment, the monitoring data includes one or more offset parameters of the corrected beam. In another illustrative embodiment, the system includes a controller communicatively coupled to the beam monitoring assembly and the beam steering assembly. In another illustrative embodiment, the controller includes one or more processors configured to execute a set of program instructions stored in memory. In another illustrative embodiment, the program instructions are configured to cause the one or more processors to store one or more zero parameters of the corrected beam. In another illustrative embodiment, the program instructions are configured to cause the one or more processors to calculate at least one difference between the one or more zero parameters and the one or more offset parameters of the corrected beam. In another illustrative embodiment, the program instructions are configured to cause the one or more processors to determine one or more beam position adjustments of the incident beam based on the at least one difference between the one or more zero parameters and the one or more offset parameters of the corrected beam. In another illustrative embodiment, the program instructions are configured to cause the one or more processors to direct the beam steering assembly, via one or more motor drivers, to actuate one or more motors to adjust the incident beam to form the corrected beam.

A method is disclosed, in accordance with one or more embodiments of the present disclosure. In one embodiment, the method may include, but is not limited to, receiving an incident beam. In another embodiment, the method may include, but is not limited to, adjusting the incident beam to form a corrected beam via a beam steering assembly. In another embodiment, the method may include, but is not limited to, generating monitoring data for the corrected beam. In another illustrative embodiment, the monitoring data includes one or more offset parameters of the corrected beam, via a beam monitoring assembly. In another embodiment, the method may include, but is not limited to, storing one or more zero parameters of the corrected beam. In another embodiment, the method may include, but is not limited to, calculating at least one difference between the one or more zero parameters and the one or more offset parameters of the corrected beam. In another embodiment, the method may include, but is not limited to, determining one or more beam position adjustments of the incident beam based on the at least one difference between the one or more zero parameters and the one or more offset parameters of the corrected beam. In another embodiment, the method may include, but is not limited to, directing the beam steering assembly, via one or more motor drivers, to actuate one or more motors based on the one or more beam position adjustments to adjust the incident beam to form the corrected beam.

It is to be understood that both the foregoing general description and the following detailed description are exemplary and explanatory only and are not necessarily restrictive of the present disclosure. The accompanying drawings, which are incorporated in and constitute a part of the characteristic, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which:

FIG. 1A illustrates a graph of relative intensity versus beam position for a

Gaussian illumination beam profile, in accordance with one or more embodiments of the present disclosure.

Figure 1A:
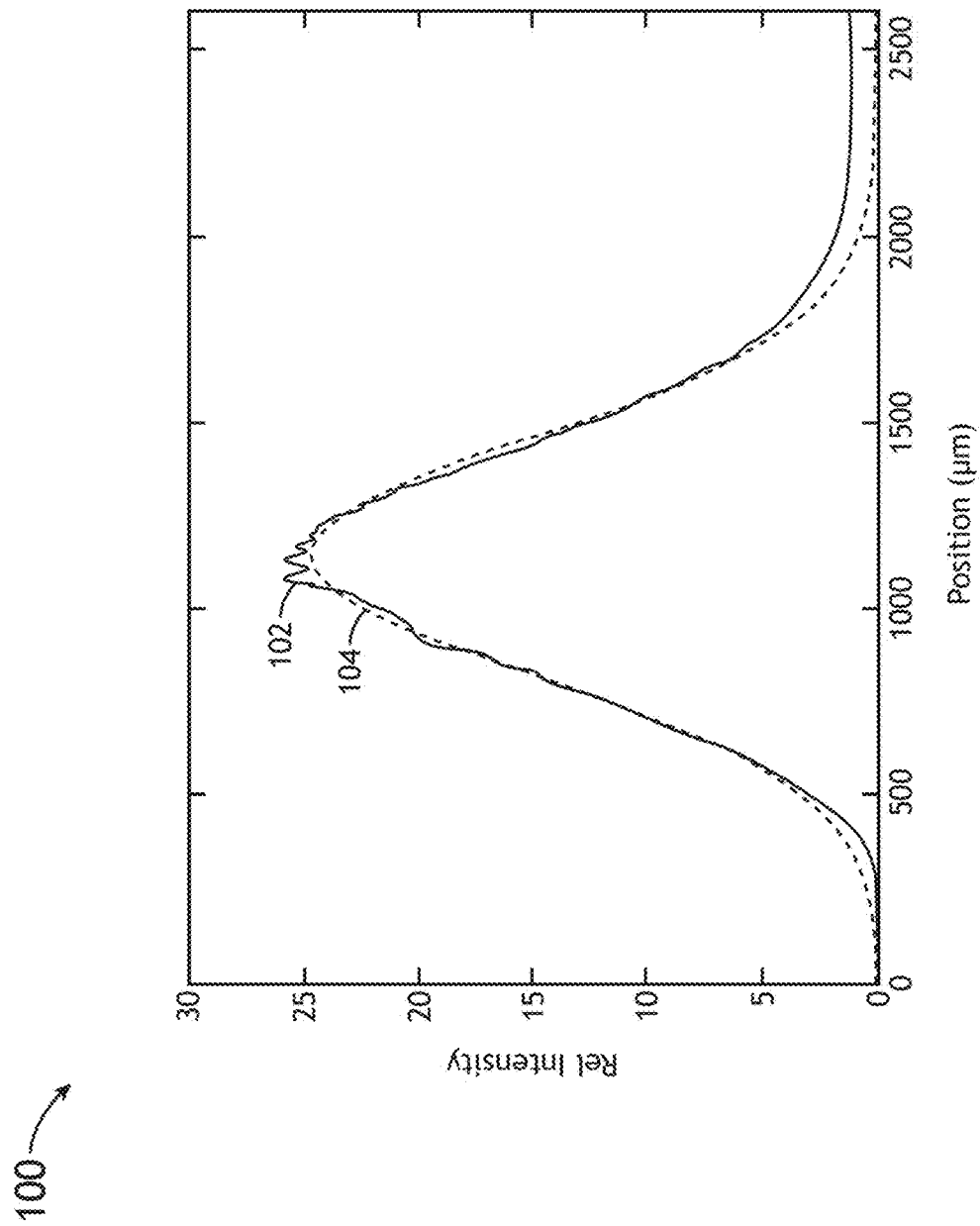
Figure 1B:
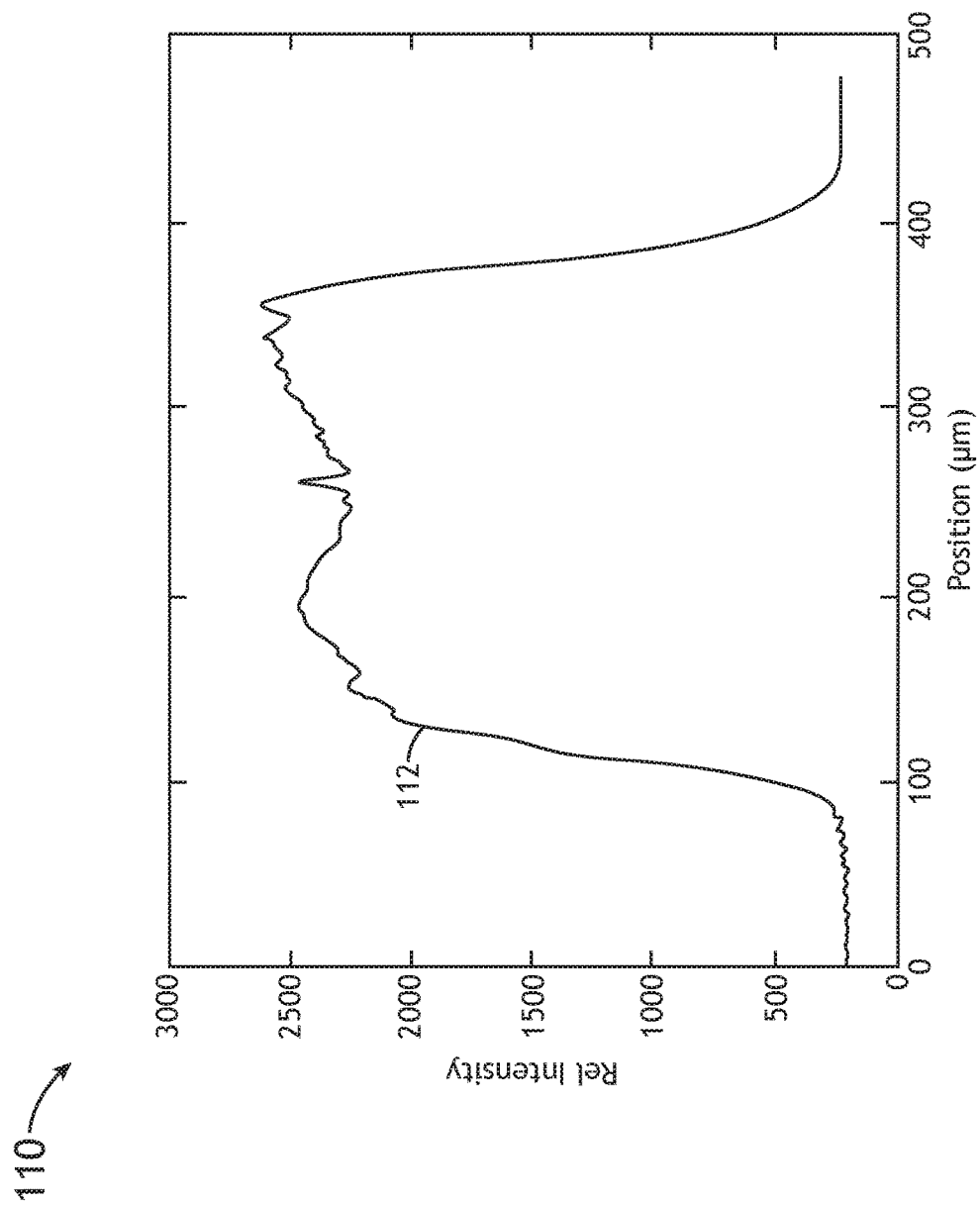

FIG. 1B illustrates a graph of relative intensity versus beam position for a flat-top illumination beam profile generated by a beam modulator from a Gaussian illumination beam, in accordance with one or more embodiments of the present disclosure.

FIG. 1C illustrates a graph of relative intensity versus beam position for a modeled flat-top illumination beam profile generated by a beam modulator from an offset Gaussian illumination beam, in accordance with one or more embodiments of the present disclosure.

Figure 1D:
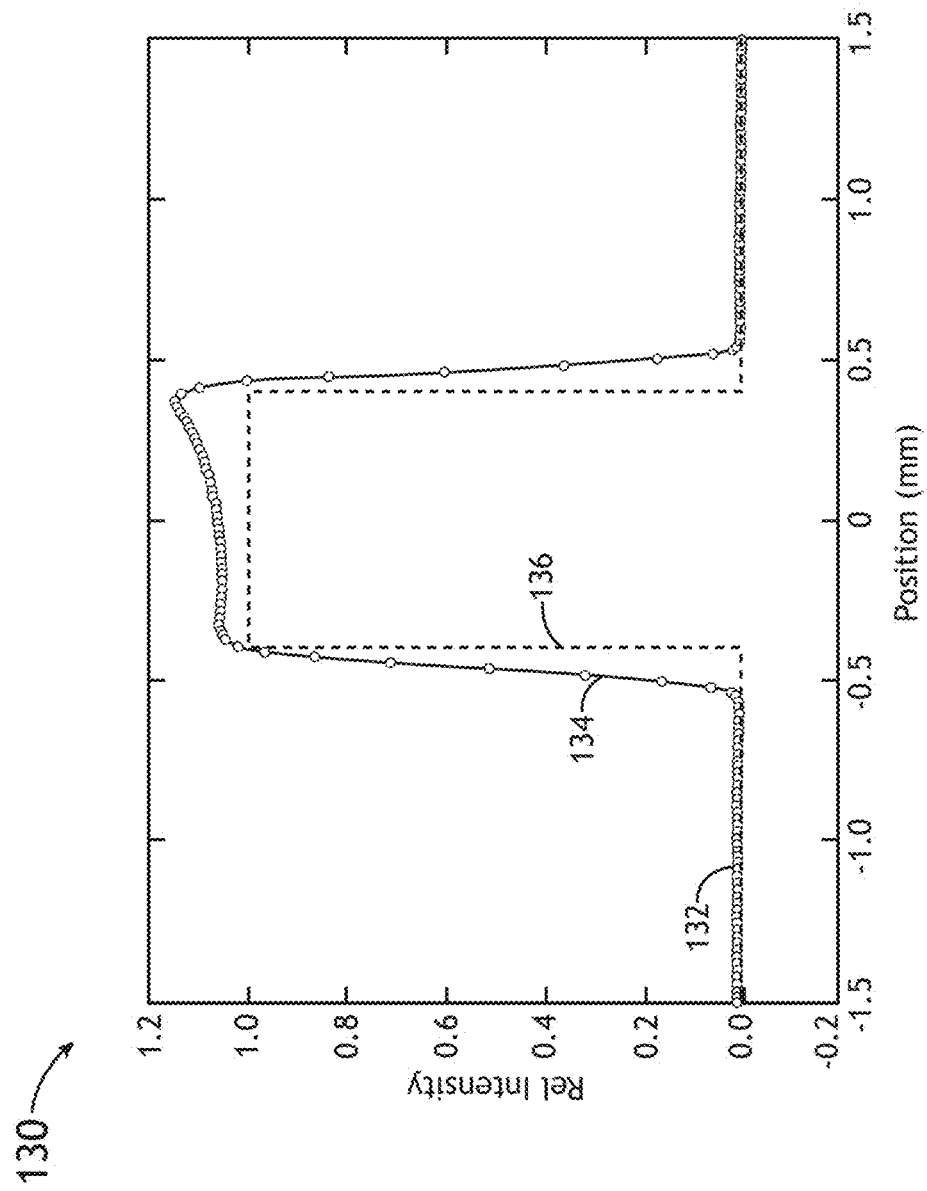

FIG. 1D illustrates a graph of relative intensity versus beam position for a modeled flat-top illumination beam profile generated by a beam modulator from an offset Gaussian illumination beam, in accordance with one or more embodiments of the present disclosure.

Figure 1E:
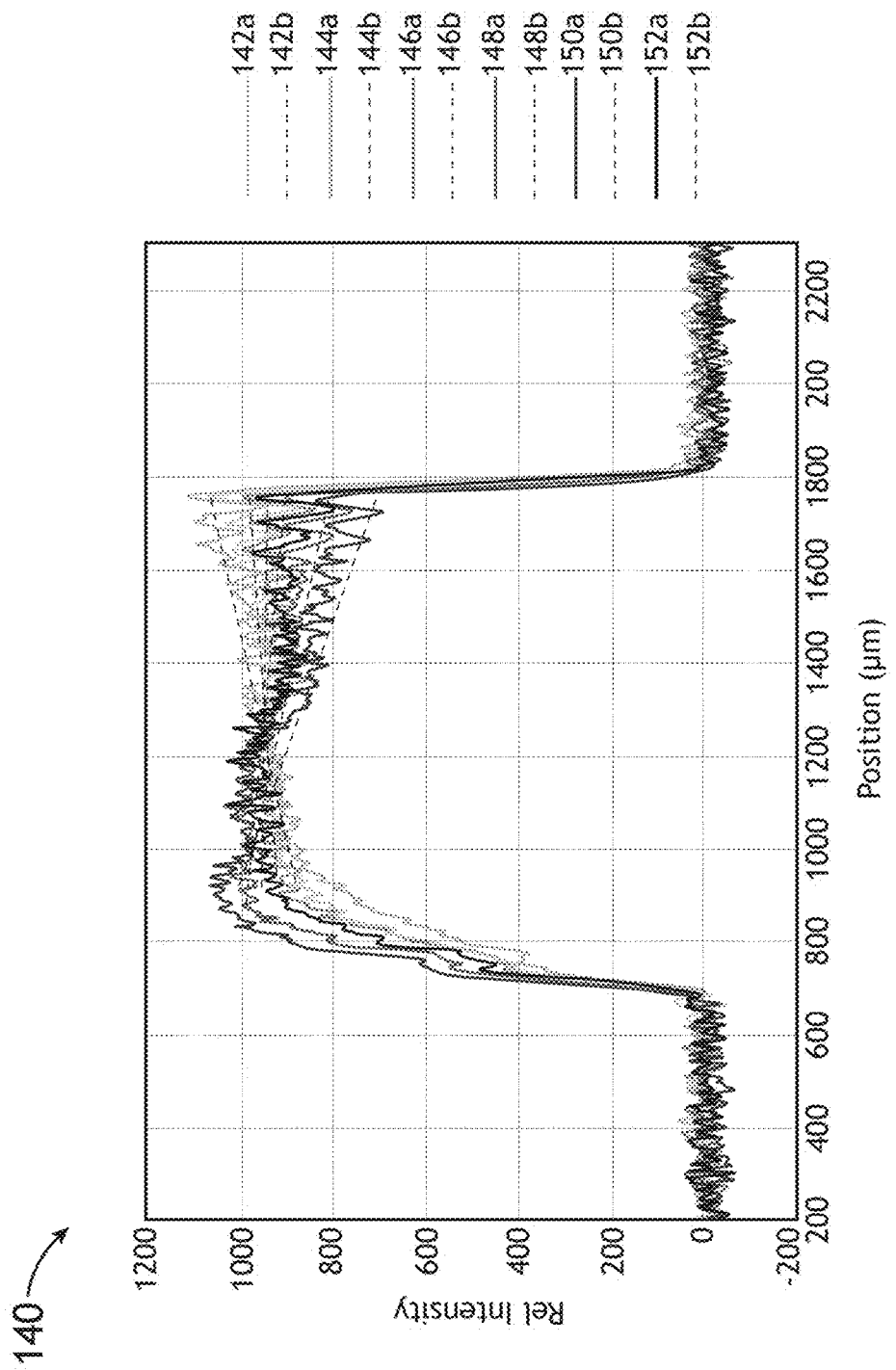

FIG. 1E illustrates a graph of relative intensity versus beam position for multiple flat-top illumination beam profiles generated by a beam modulator from multiple off-centered Gaussian illumination beams, in accordance with one or more embodiments of the present disclosure.

Figure 1F:
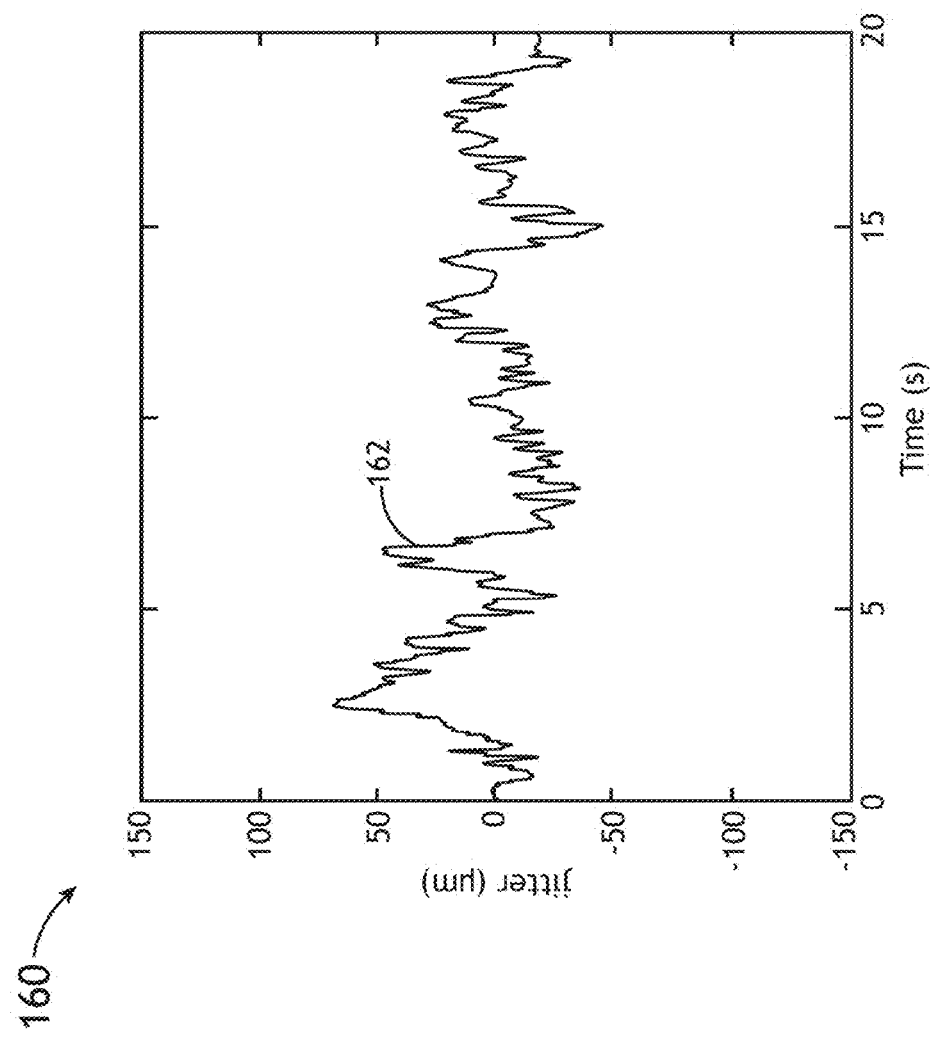

FIG. 1F illustrates a graph of jitter measured as a function of time within an inspection system, in accordance with one or more embodiments of the present disclosure.

Figure 1G:
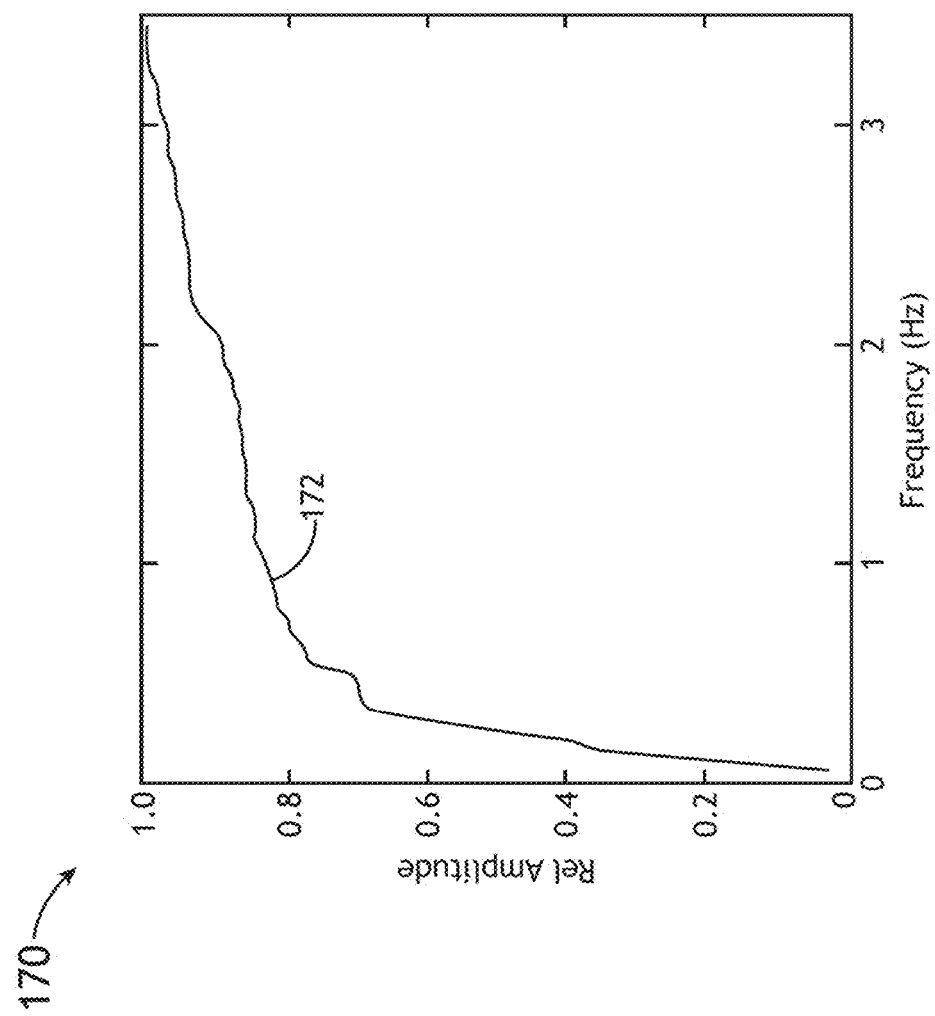

FIG. 1G illustrates a graph of the relative amplitude of jitter versus the frequency of jitter within an inspection system, in accordance with one or more embodiments of the present disclosure.

Figure 2:
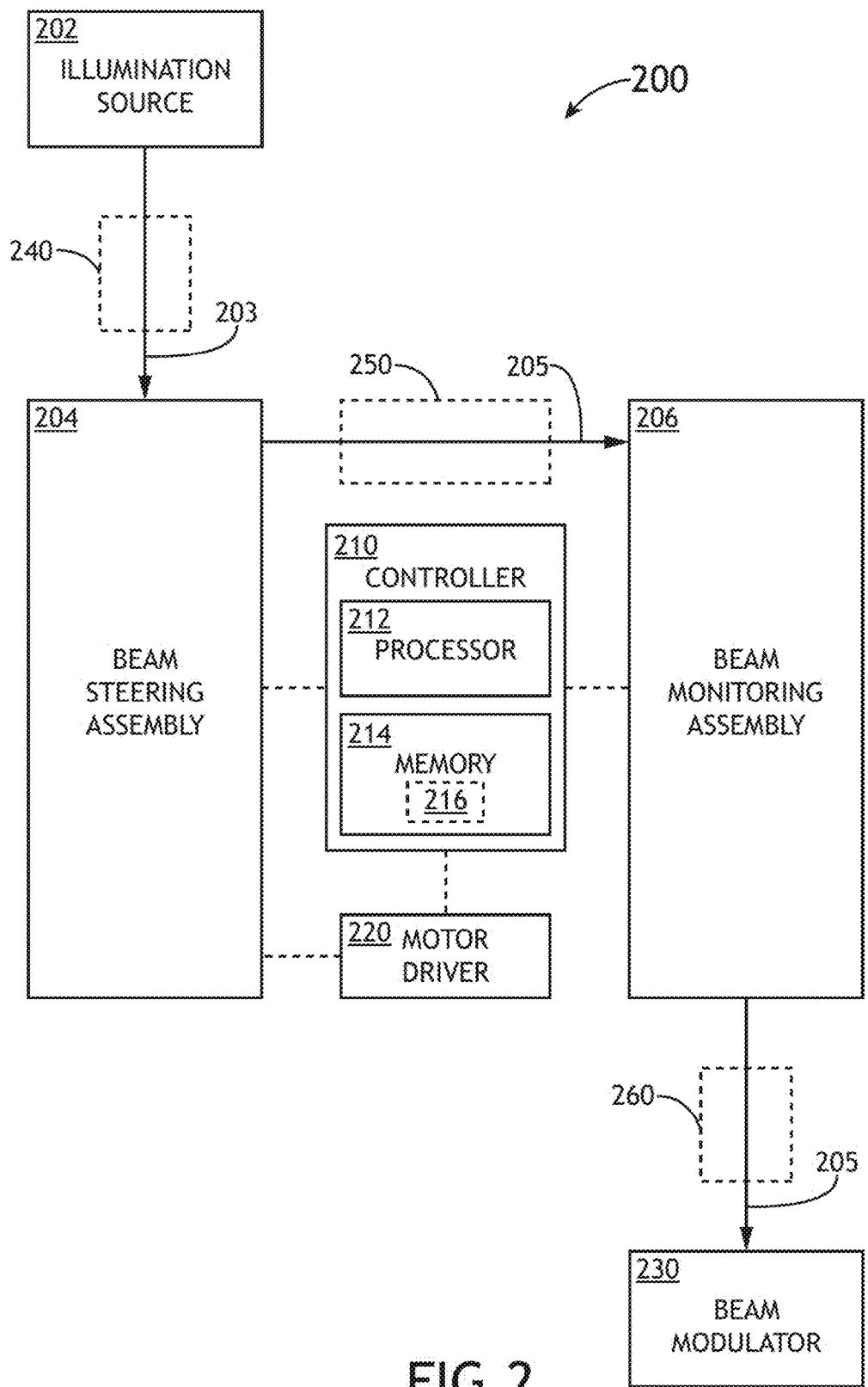

FIG. 2 illustrates a block diagram view of a system to compensate for illumination beam misalignment, in accordance with one or more embodiments of the present disclosure.

Figure 3A:
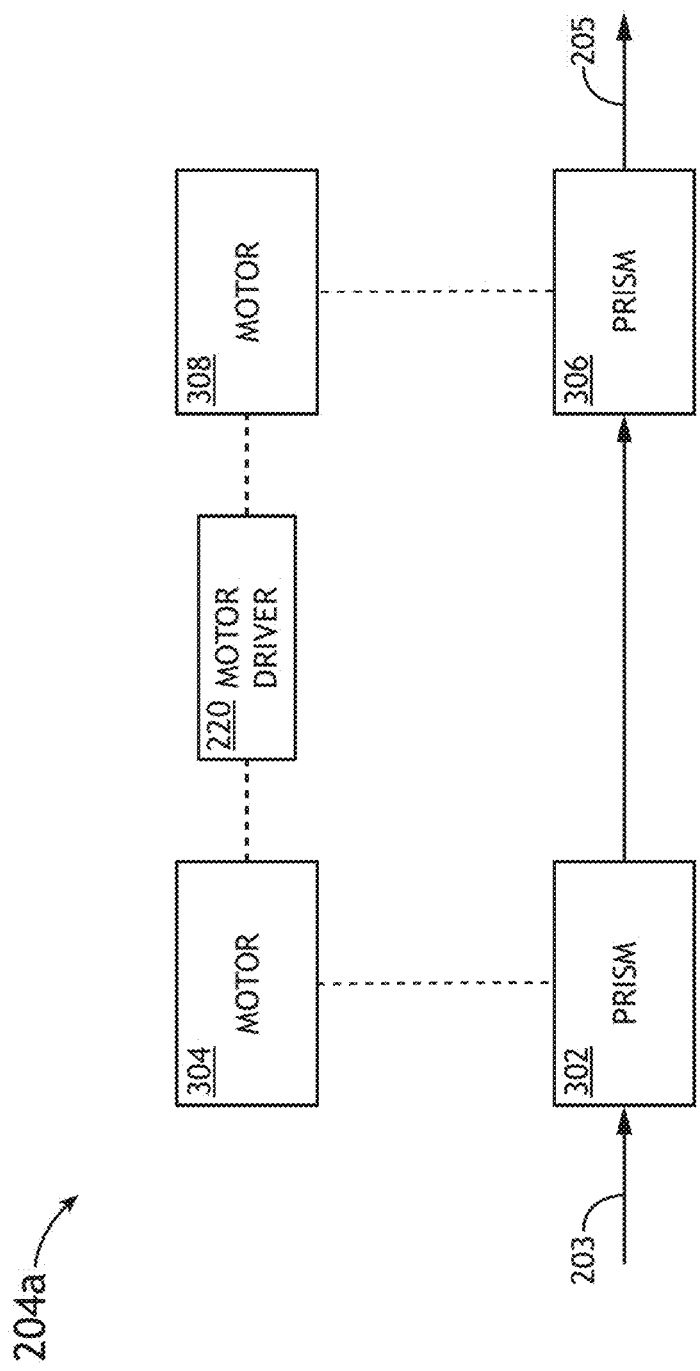

FIG. 3A illustrates a block diagram view of a beam steering assembly, in accordance with one or more embodiments of the present disclosure.

Figure 3B:
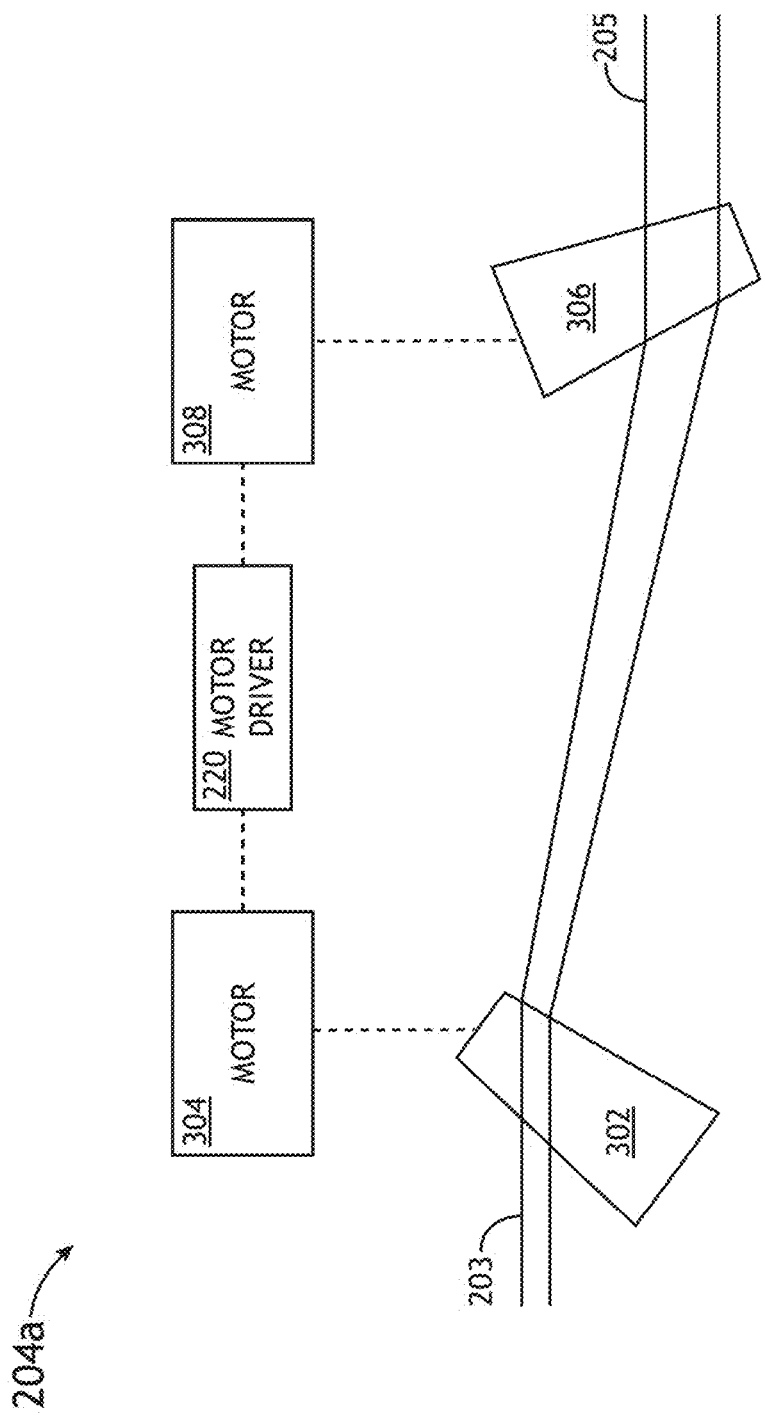

FIG. 3B illustrates a block diagram view of a beam steering assembly, in accordance with one or more embodiments of the present disclosure.

Figure 3C:
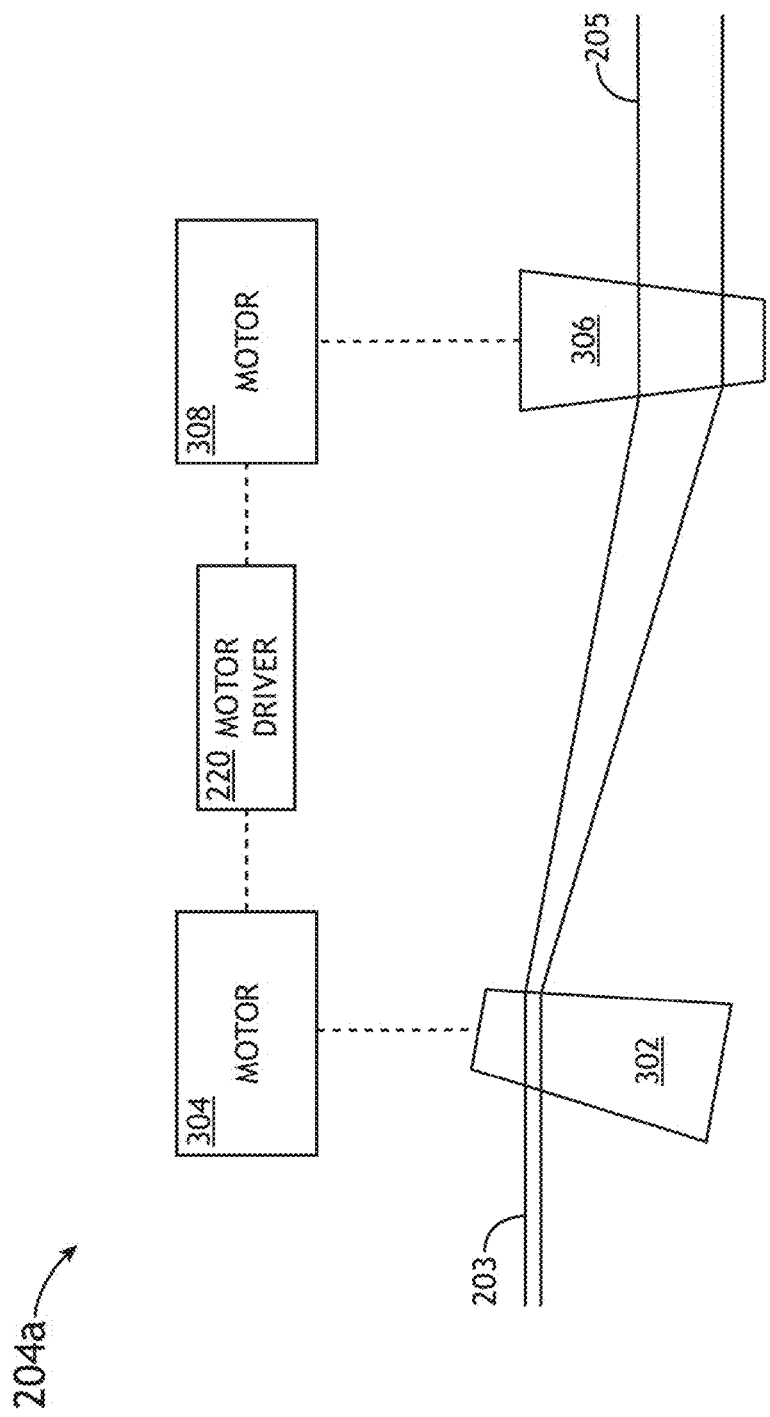

FIG. 3C illustrates a block diagram view of a beam steering assembly, in accordance with one or more embodiments of the present disclosure.

Figure 3D:
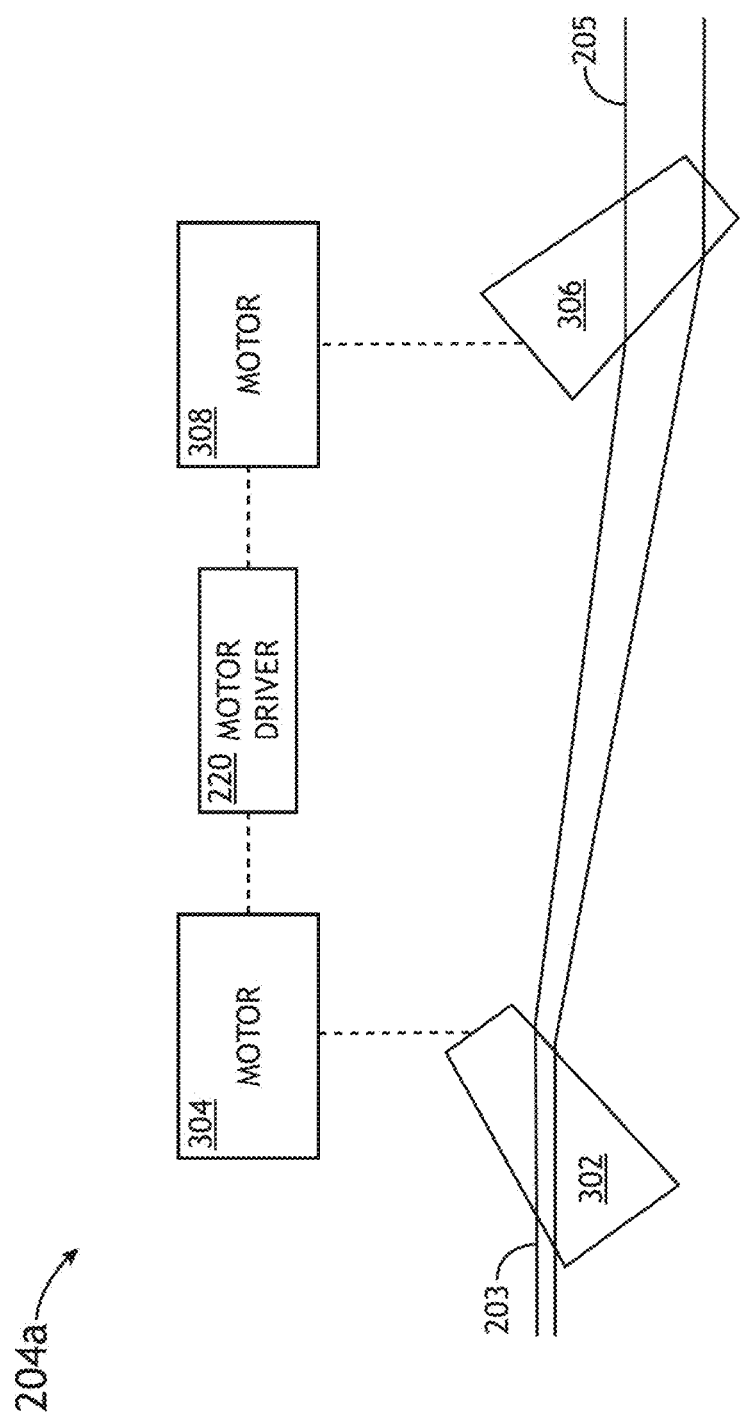

FIG. 3D illustrates a block diagram view of a beam steering assembly, in accordance with one or more embodiments of the present disclosure.

Figure 3E:
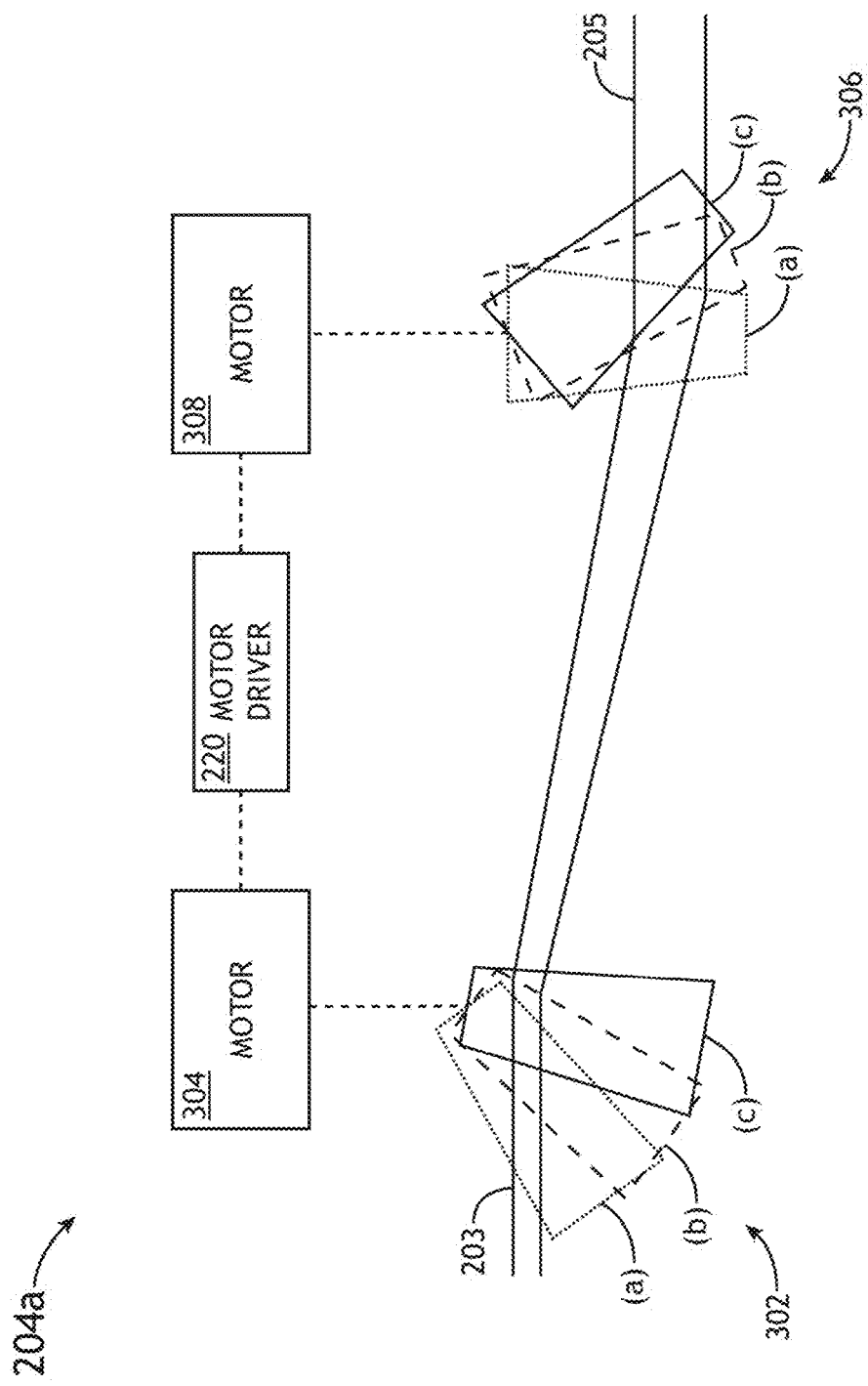

FIG. 3E illustrates a block diagram view of a beam steering assembly, in accordance with one or more embodiments of the present disclosure.

Figure 4:
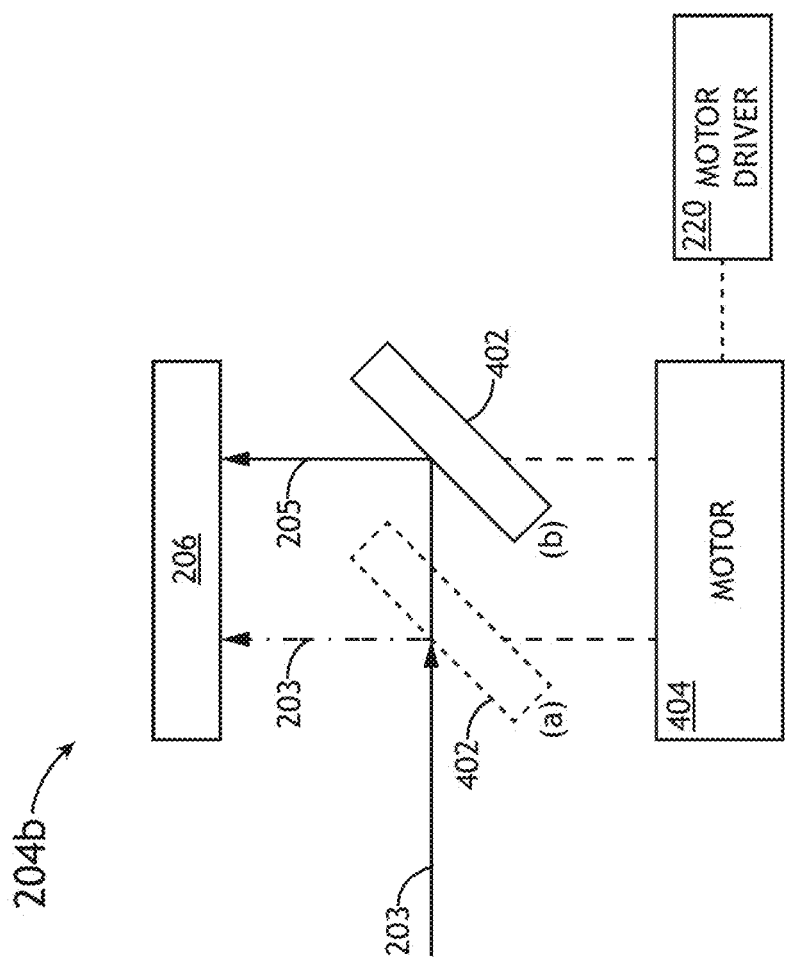

FIG. 4 illustrates a block diagram view of a beam steering assembly, in accordance with one or more embodiments of the present disclosure.

Figure 5:
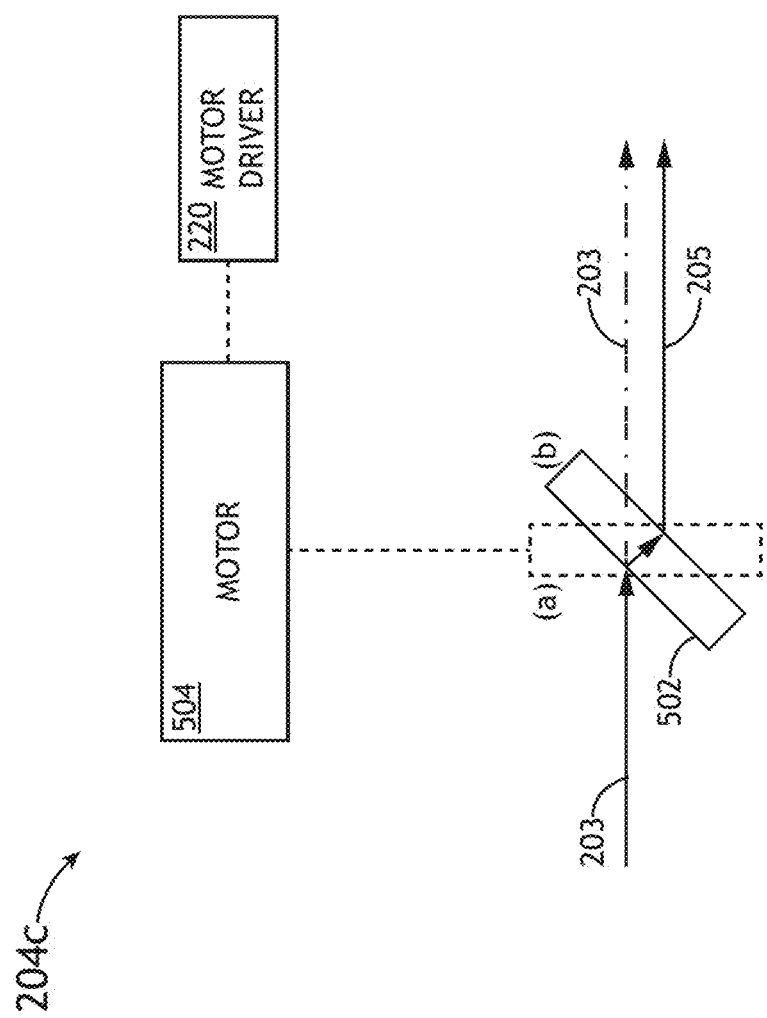

FIG. 5 illustrates a block diagram view of a beam steering assembly, in accordance with one or more embodiments of the present disclosure.

Figure 6A:
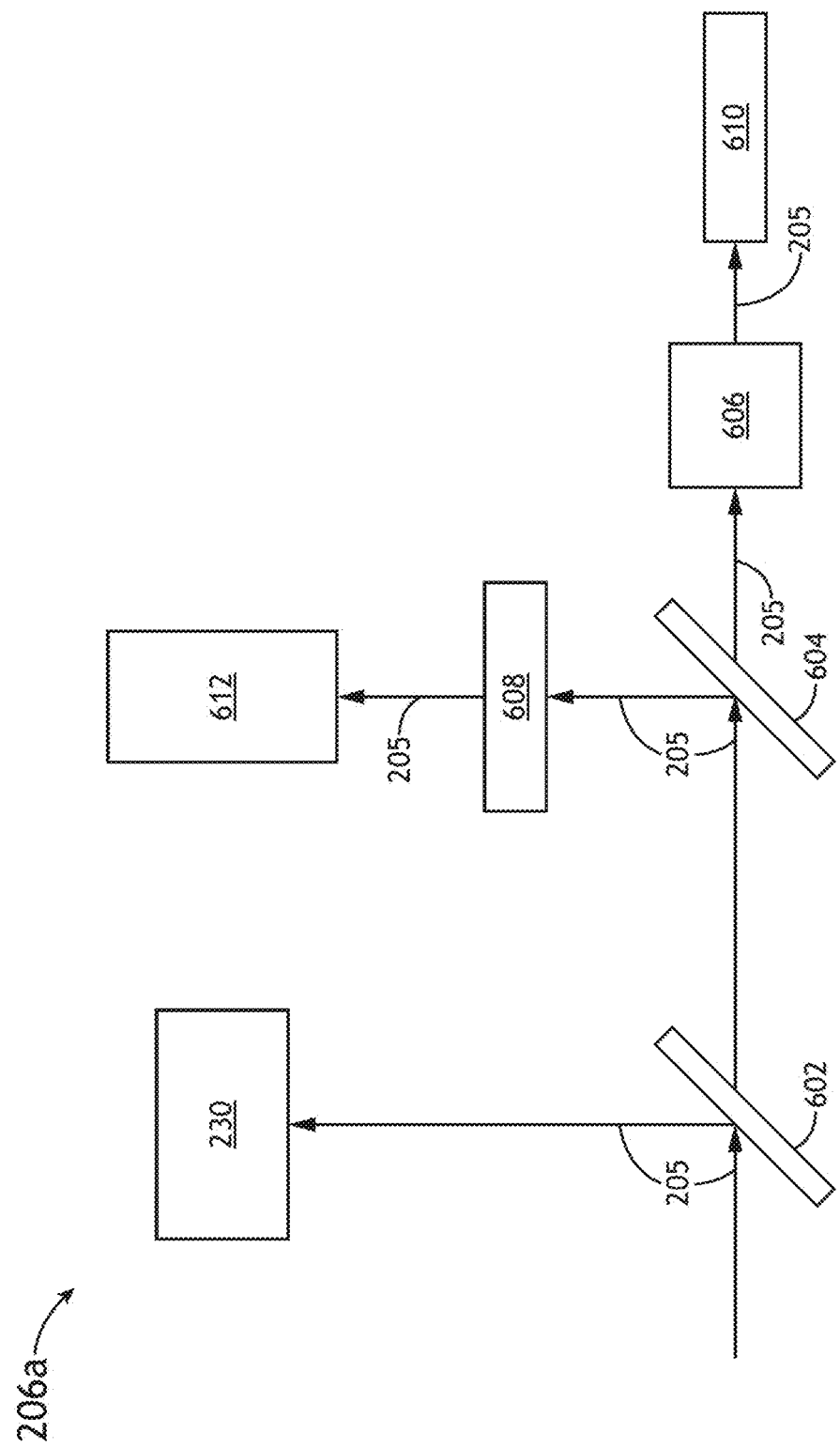

FIG. 6A illustrates a block diagram view of a beam monitoring assembly, in accordance with one or more embodiments of the present disclosure.

Figure 6B:
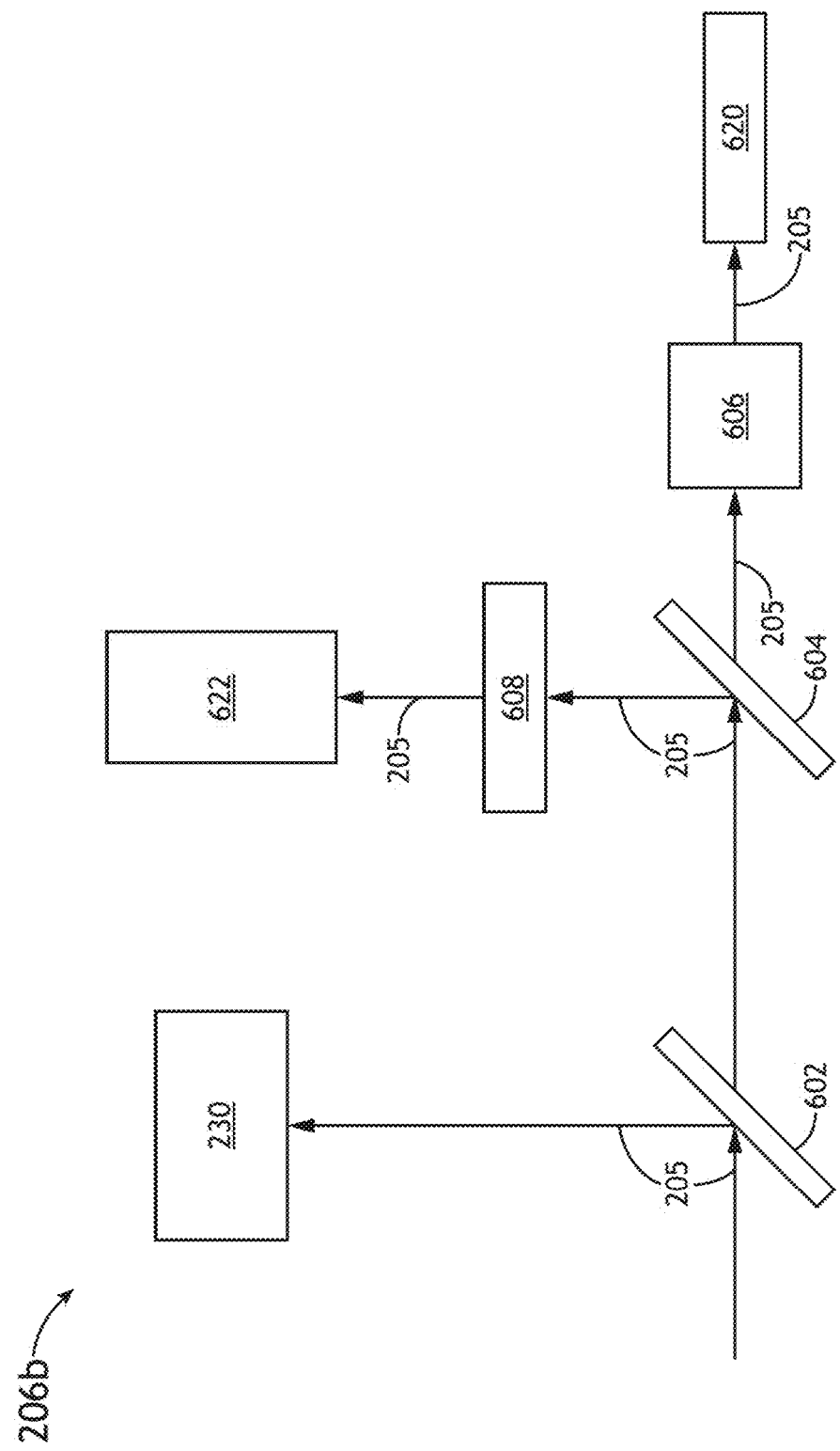

FIG. 6B illustrates a block diagram view of a beam monitoring assembly, in accordance with one or more embodiments of the present disclosure.

Figure 6C:
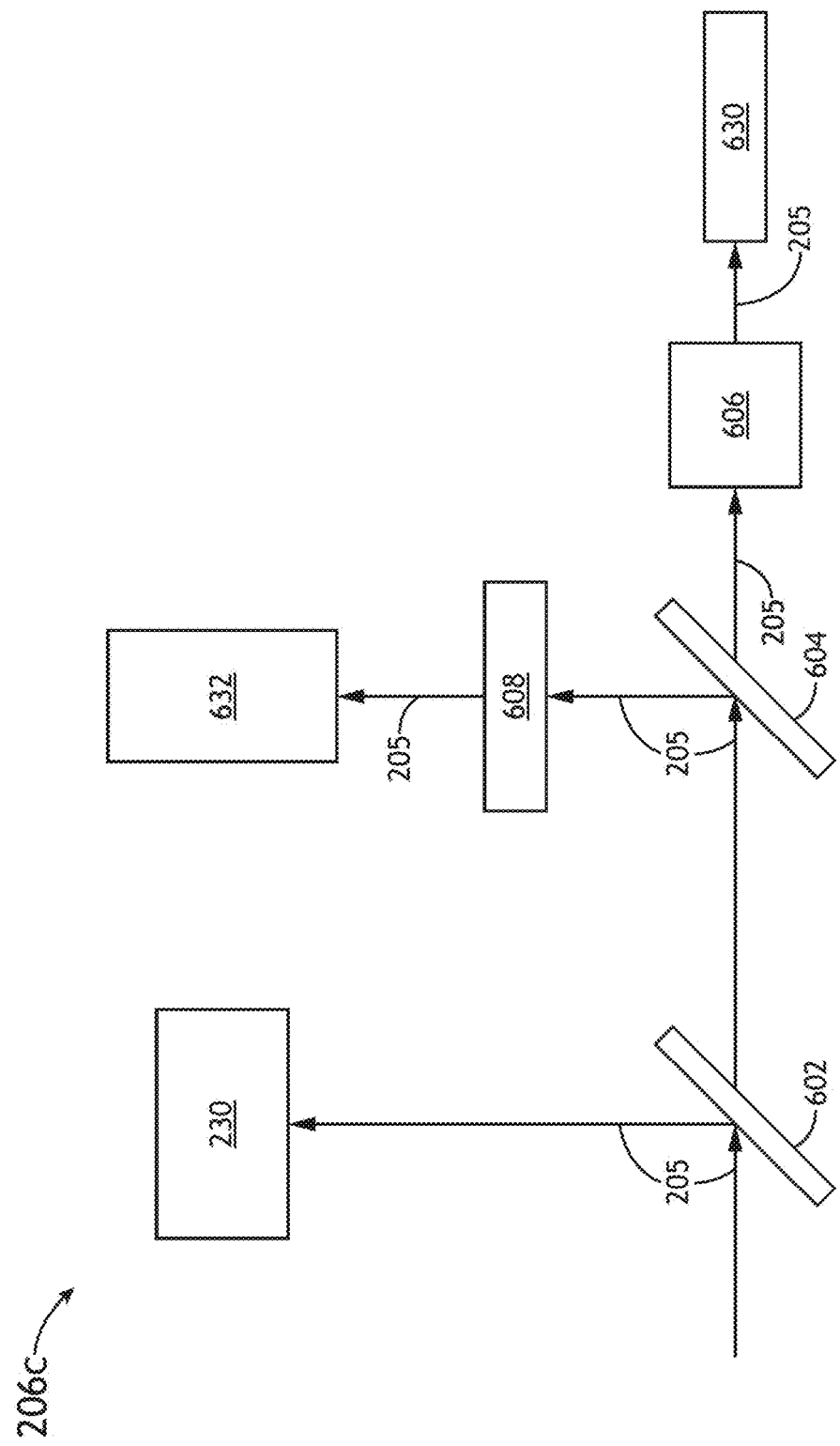

FIG. 6C illustrates a block diagram view of a beam monitoring assembly, in accordance with one or more embodiments of the present disclosure.

Figure 7:
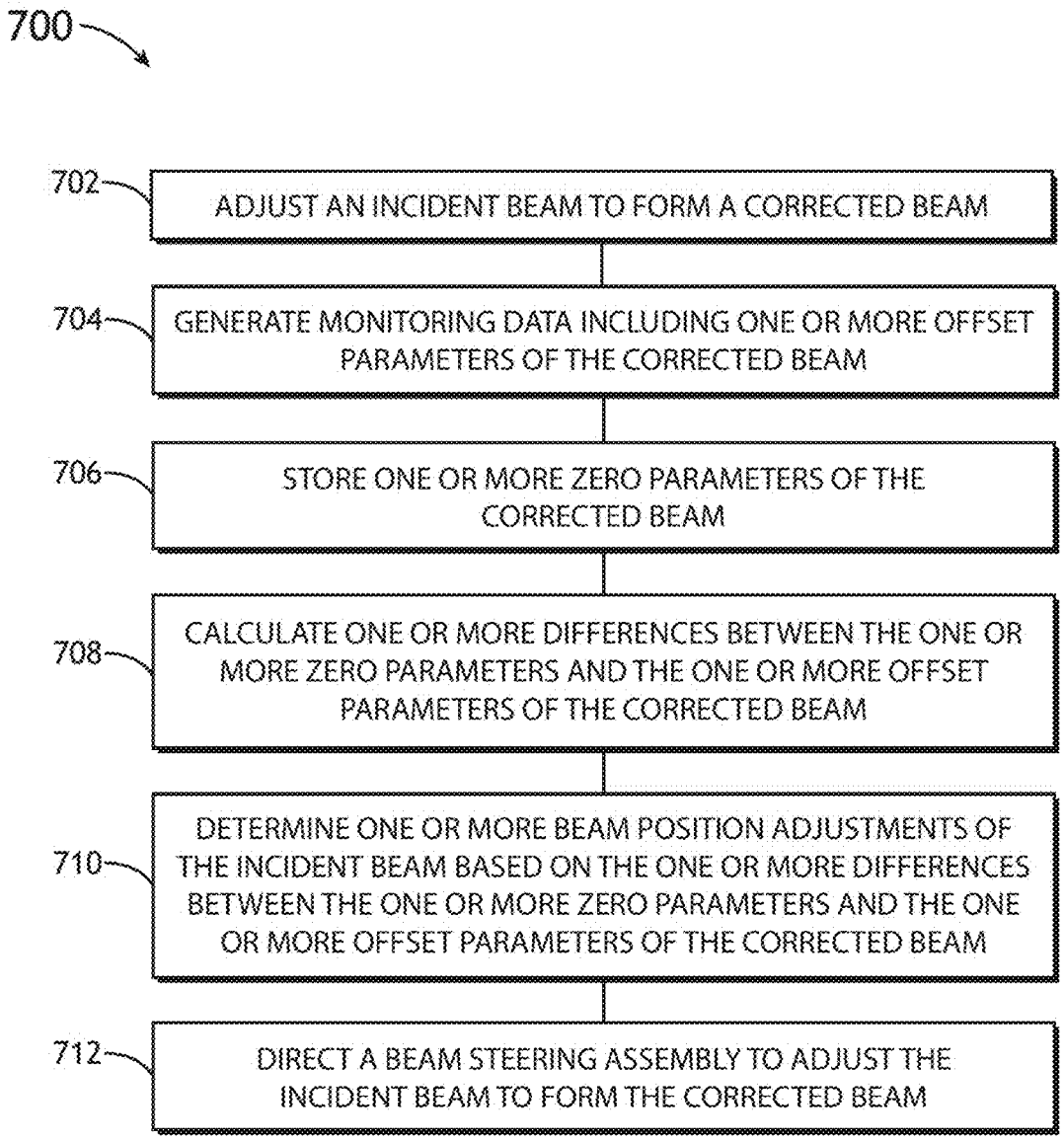

FIG. 7 illustrates a flow diagram depicting a method to compensate for illumination beam misalignment, in accordance with one or more embodiments of the present disclosure.

DETAILED DESCRIPTION OF THE INVENTION

Reference will now be made in detail to the subject matter disclosed, which is illustrated in the accompanying drawings.

Referring to FIGS. 1A through 7, a system and a method to compensate for illumination beam misalignment are disclosed, in accordance with one or more embodiments of the present disclosure.

In some instances, inspection systems implement an illumination beam focused at the Gaussian beam focal plane. Being focused at the focal plane, these inspection systems observe only a minimal impact of the illumination beam position from translational jitter in the inspection system. FIG. 1A illustrates a graph 100 of relative intensity versus beam position (in μm) for a Gaussian illumination beam profile, with data 102 and a fit curve 104.

Improved inspection systems instead implement a flat-top illumination beam formed by passing a Gaussian illumination beam through a beam modulator. FIG. 1B illustrates a graph 110 of relative intensity versus beam position (in μm) for a flat-top illumination beam profile, with data 112.

The quality of a flat-top illumination beam profile is correlated with the position of the Gaussian beam on the beam modulator. If the Gaussian beam is offset from center, the flat-top profile will have an unwanted tilt feature on the edge of the flat-top profile in the direction of the offset. FIG. 1C illustrates a graph 120 of relative intensity versus beam position (in mm) for a modeled flat-top illumination beam profile generated by a beam modulator from an Gaussian illumination beam offset by −0.1 mm, with data 122, a fit curve 124, and a comparison curve 126. FIG. 1D illustrates a graph 130 of relative intensity versus beam position (in mm) for a modeled flat-top illumination beam profile generated by a beam modulator from an Gaussian illumination beam offset by +0.1 mm, with data 132, a fit curve 134, and a comparison curve 136.

Any pointing or translational jitter in the input Gaussian illumination beam will be exhibited on the beam modulator in real-time, with the flat-top profile rocking on its edges with a frequency similar to the frequency of the pointing or translational jitter in the input Gaussian illumination beam. FIG. 1E illustrates a graph 140 of relative intensity versus beam position for multiple modeled flat-top illumination beam profiles generated by a beam modulator from multiple offset Gaussian illumination beams. For example, data 142a and a fit curve 142b illustrate a beam offset of −150 μm. By way of another example, data 144a and a fit curve 144b illustrate a beam offset of −300 μm. By way of another example, data 146a and a fit curve 146b illustrate a beam offset of −50 μm. By way of another example, data 148a and a fit curve 148b illustrate a beam offset of 150 μm. By way of another example, data 150a and a fit curve 150b illustrate a beam offset of 300 μm. By way of another example, data 152a and a fit curve 152b illustrate a beam offset of 50 μm.

Approximately 99% of jitter in the improved inspection systems is >100 μm at the critical optical plane, which results in a sizing instability that impacts inspection system signal stability and capture rate. FIG. 1F illustrates a graph 160 of jitter (in μm) measured as a function of time (in sec) within an inspection system, with data 162. FIG. 1G illustrates a graph 170 of the relative amplitude of jitter versus the frequency of jitter (in Hz) within an inspection system, with data 172.

As such, it would be desirable to provide an improved inspection system with the capability to reduce system jitter by compensating for the misalignment of the illumination beam. For example, it would be desirable for the improved inspection system to be capable of reducing system jitter by approximately 10×.

Embodiments of the present disclosure are directed to a system and a method to compensate for illumination beam misalignment. Embodiments of the present disclosure are also directed to measuring one or more of the following: a translational component of the position of an illumination beam, a pointing component of the position of the illumination beam, an illumination beam size, and/or illumination beam breathing data. Embodiments of the present disclosure are also directed to determining one or more illumination beam adjustments based on measured data. Embodiments of the present disclosure are also directed to forming a corrected illumination beam by adjusting one or more of the following: a translation component of a position of the illumination beam, a pointing component a position of the illumination beam, a drift in the size of the illumination beam, and/or a variance in the illumination beam breathing data. Embodiments of the present disclosure are also directed to measuring the illumination beam, determining adjustments for the illumination beam, and adjusting an illumination beam to form the corrected beam in one or more of an x-direction and/or a y-direction.

FIG. 2 illustrates a block diagram view of a system 200 to compensate for illumination beam misalignment, in accordance with one or more embodiments of the present disclosure. In one embodiment, the system 200 includes an illumination source 202. In another embodiment, the system 200 includes a beam steering assembly 204. In another embodiment, the system 200 includes a beam monitoring assembly 206. In another embodiment, the system 200 includes a controller 210. In another embodiment, the system 200 includes one or more motor drivers 220. In another embodiment, the system 200 includes a beam modulator 230.

The illumination source 202 may include any illumination source known in the art including, but not limited to, a broadband light source or a narrowband light source. In one embodiment, the illumination source 202 includes one or more lasers. For example, the illumination source 202 may include any laser or laser system known in the art capable of emitting radiation in the infrared, visible and/or ultraviolet portions of the electromagnetic spectrum. For instance, the illumination source 202 may include, but is not limited to, one or more diode lasers, one or more continuous wave (CW) lasers, one or more ion lasers, and the like.

In one embodiment, the illumination source 202 generates an incident beam 203. In another embodiment, the beam steering assembly 204 is optically coupled to the illumination source 202. In this regard, the illumination source 202 generates the incident beam 203 and directs the incident beam 203 to the beam steering assembly 204. For example, the illumination source 202 may direct the incident beam 203 to the beam steering assembly 204 through an optical element assembly 240. For instance, the optical element assembly 240 may include one or more optical elements known in the optical arts such as, but not limited to, steering optics, mirrors, beam splitters, lenses, collecting apertures, filters, and the like.

In another embodiment, the beam steering assembly 204 adjusts the incident beam 203 to form a corrected beam 205. In another embodiment, the beam monitoring assembly 206 is optically coupled to the beam steering assembly 204. In another embodiment, the beam steering assembly 204 directs the corrected beam 205 to the beam monitoring assembly 206. For example, the beam steering assembly 204 may direct the corrected beam 205 to the beam monitoring assembly 206 through an optical element assembly 250. For instance, the optical element assembly 250 may include one or more optical elements known in the optical arts such as, but not limited to, steering optics, mirrors, beam splitters, lenses, collecting apertures, filters, and the like.

In another embodiment, the beam steering assembly 204 is communicatively coupled to one or more of the controller 210 and the one or more motor drivers 220.

In another embodiment, the beam monitoring assembly 206 directs at least a portion of the corrected beam 205 to the beam modulator 230. For example, the beam modulator 230 may include, but is not limited to, a beam shaping optical element. For instance, the beam shaping optical element may include, but is not limited to, a multi-curved lens or a diffractive optical element. By way of another example, the beam monitoring assembly 206 may direct the corrected beam 205 to the beam modulator 230 through an optical element assembly 260. For instance, the optical element assembly 260 may include one or more optical elements known in the optical arts such as, but not limited to, steering optics, mirrors, beam splitters, lenses, collecting apertures, filters, and the like.

In another embodiment, the beam monitoring assembly 206 is communicatively coupled to the controller 210. In another embodiment, the beam monitoring assembly 206 generates one or more sets of monitoring data for the corrected beam 205. For example, the one or more sets of monitoring data are generated via one or more beam monitoring sensors. For instance, the one or more beam monitoring sensors may include, but are not limited to, one or more cameras or one or more bi-cell detectors, described in detail further herein.

In another embodiment, the one or more sets of monitoring data include one or more offset parameters of the corrected beam 205. For example, the one or more offset parameters may include, but are not limited to, an offset pointing component of an offset position of the corrected beam 205. By way of another example, the one or more offset parameters may include, but are not limited to, an offset translation component of the offset position of the corrected beam 205. By way of another example, the one or more offset parameters may include, but are not limited to, an offset beam size. By way of another example, the one or more offset parameters may include, but are not limited to, offset beam breathing data. In another embodiment, the one or more offset parameters of the corrected beam 205 includes one or more of an x-direction component and/or a y-direction component. In another embodiment, the beam monitoring assembly 206 transmits the one or more sets of monitoring data for the corrected beam 205 to the controller 210.

In one embodiment, the one or more motor drivers 220 are communicatively coupled to one or more of the beam steering assembly 204 and the controller 210. In another embodiment, the one or more motor drivers 220 actuate one or more motors in the beam steering assembly 204 based on one or more beam position adjustments received from the controller 210, as described in detail further herein.

In another embodiment, the beam steering assembly 204 includes one or more encoders. In another embodiment, the encoders generate data following actuation of the one or more motors. In another embodiment, the beam steering assembly 204 aggregates the generated encoder data prior to transmission to the controller 210, and the controller 210 de-aggregates the aggregated encoder data upon receipt. In another embodiment, the system 200 receives the generated encoder data in a non-aggregated form.

In one embodiment, the controller 210 includes one or more processors 212 and a memory medium 214. In another embodiment, one or more sets of program instructions 216 are stored in memory medium 214. In another embodiment, the one or more processors 212 are configured to execute the sets of program instructions 216 to carry out one or more of the various steps described throughout the present disclosure.

In another embodiment, the controller 210 is communicatively coupled to one or more of the beam steering assembly 204, the beam monitoring assembly 206, and the one or more motor drivers 220. In another embodiment, the controller 210 is configured to receive and/or acquire data or information from other systems or assemblies (e.g., the one or more sets of monitoring data from the beam monitoring assembly 206, one or more sets of encoder data from the beam steering assembly 204, or one or more user inputs received via a user interface) by a transmission medium that may include wireline and/or wireless portions. In another embodiment, the controller 210 of the system 200 is configured to transmit data or information (e.g., the output of one or more procedures disclosed herein) to one or more systems or assemblies (e.g., one or more commands to the one or more motor drivers 220, the beam steering assembly 204, the beam monitoring assembly 206, or a user interface) by a transmission medium that may include wireline and/or wireless portions. In this regard, the transmission medium may serve as a data link between the controller 210 and other assemblies of the system 200. In another embodiment, the controller 210 is configured to send data to external systems via a transmission medium (e.g., network connection).

In one embodiment, the set of program instructions 216 are programmed to cause the one or more processors 212 to store one or more zero parameters for the corrected beam 206. For example, the one or more zero parameters may include, but are not limited to, a zero pointing component of a zero position of the corrected beam 205. By way of another example, the one or more zero parameters may include, but are not limited to, a zero translation component of the zero position of the corrected beam 205. By way of another example, the one or more zero parameters may include, but are not limited to, a zero beam size. By way of another example, the one or more zero parameters may include, but are not limited to, zero beam breathing data. In another embodiment, the one or more zero parameters of the corrected beam 205 include one or more of an x-direction component and/or a y-direction component.

In another embodiment, the set of program instructions 216 are programmed to cause the one or more processors 212 to receive the one or more sets of monitoring data from the beam monitoring assembly 206. In another embodiment, the controller 210 calculates one or more differences between the one or more zero parameters and the one or more offset parameters of the corrected beam 205. For example, calculating the one or more differences may include calculating a pointing difference between the zero pointing component of the zero position of the corrected beam 205 and the offset pointing component of the offset position of the corrected beam 205. By way of another example, calculating one or more differences may include calculating a translation difference between the zero translation component of the zero position of the corrected beam 205 and the offset translation component of the offset position of the corrected beam 205. By way of another example, calculating one or more differences may include calculating a beam size difference between the zero beam size and the offset beam size. By way of another example, calculating one or more differences may include calculating a beam breathing data difference between the zero beam breathing data and the offset beam breathing data.

In another embodiment, the set of program instructions 216 are programmed to cause the one or more processors 212 to determine one or more beam position adjustments of the incident beam 203 based on the calculated one or more differences between the one or more zero parameters and the one or more offset parameters of the corrected beam 205. In another embodiment, the controller 210 transmits the one or more beam position adjustments to the one or more motor drivers 220.

In another embodiment, the set of program instructions 216 are programmed to cause the one or more processors 212 to direct the beam steering assembly 204, via the one or more motor drivers 220, to actuate one or more motors and adjust the incident beam 203 to form the corrected beam 205. For example, the one or more motors drivers 220 may adjust the incident beam 203 based on the one or more beam position adjustments. For instance, the one or more beam position adjustments may include one or more commands to actuate the one or more motors coupled to one or more optical components of the beam steering assembly 204, described in detail further herein.

In another embodiment, the set of program instructions 216 are programmed to cause the one or more processors 212 to verify the actuation of the one or more motors based on generated encoder data received from the beam steering assembly 204.

In one embodiment, the one or more processors 212 of controller 210 include any one or more processing elements known in the art. In this sense, the one or more processors 212 may include any microprocessor device configured to execute algorithms and/or instructions. For example, the one or more processors 212 may consist of a desktop computer, mainframe computer system, workstation, image computer, parallel processor, vehicle on-board computer, handheld computer (e.g. tablet, smartphone, or phablet), or other computer system (e.g., networked computer) configured to execute a program configured to operate the system 200, as described throughout the present disclosure. It should be recognized that the steps described throughout the present disclosure may be carried out by a single computer system or, alternatively, multiple computer systems. The term "processor" may be broadly defined to encompass any device having one or more processing elements, which execute the program instructions 216 from a non-transitory memory medium (e.g., memory 214). Moreover, different assemblies of the system 200 (e.g., the beam steering assembly 204, the beam monitoring assembly 206, the one or more motor drivers 220, or a user interface) may include processor or logic elements suitable for carrying out at least a portion of the steps described throughout the present disclosure. Therefore, the above description should not be interpreted as a limitation on the present disclosure but merely an illustration.

In one embodiment, the memory medium 214 of controller 210 includes any memory medium known in the art suitable for storing the program instructions 216 executable by the associated one or more processors 212. For example, the memory medium 214 may include a non-transitory memory medium. For instance, the memory medium 214 may include, but is not limited to, a read-only memory, a random access memory, a magnetic or optical memory device (e.g., disk), a magnetic tape, a solid state drive and the like. In another embodiment, it is noted herein that the memory 214 is configured to provide display information to a display device and/or the output of the various steps described herein. It is further noted that memory 214 may be housed in a common controller housing with the one or more processors 212. In an alternative embodiment, the memory 214 may be located remotely with respect to the physical location of the processors 212 and controller 210. For instance, the one or more processors 212 of controller 210 may access a remote memory (e.g., server), accessible through a network (e.g., internet, intranet and the like). In another embodiment, the memory medium 214 stores the program instructions 216 for causing the one or more processors 212 to carry out the various steps described through the present disclosure.

In additional embodiments, the system 200 includes a user interface. In another embodiment, the user interface is communicatively coupled to the one or more processors 212 of controller 210. In another embodiment, the user interface includes a display device (e.g., a liquid crystal display (LCD), an organic light emitted diode (OLED) display, a cathode-ray tube (CRT) display, and the like). In another embodiment, the user interface includes a user input device (e.g., a keyboard, a mouse, a touch screen, and the like).

In additional embodiments, the system 200 may include a stage configured to secure a sample. In another embodiment, an illumination beam generated by the beam modulator 230 illuminates the sample secured on the stage. In another embodiment, the sample includes a wafer. For example, the sample may include, but is not limited to, a semiconductor wafer. As used through the present disclosure, the term "wafer" refers to a substrate formed of a semiconductor and/or non-semi-conductor material. For instance, a semiconductor or semiconductor material may include, but are not limited to, monocrystalline silicon, gallium arsenide, and indium phosphide.

In another embodiment, the sample stage may include any appropriate mechanical and/or robotic assembly known in the art. In another embodiment, the controller 210 (or another controller in the system 200) may actuate the sample stage. For example, the sample stage may be configured by the controller 210 (or another controller in the system 200) to actuate the sample to a selected position or orientation. For instance, the sample stage may include or may be mechanically coupled to one or more actuators including, but not limited to, a motor or servo, where the one or more actuators are configured to translate or rotate the sample for positioning, focusing, and/or scanning in accordance with a selected inspection or metrology algorithm, several of which are known to the art.

In additional embodiments, the system 200 may include one or more optical components configured to direct illumination reflected and/or scattered from the surface of the sample to one or more detectors. For example, the detectors may include any appropriate detector known in the art. For instance, the detectors may include, but is not limited to, one or more photo-multiplier tubes (PMTs), charge coupled devices (CCDs), time delay integration (TDI) camera, and the like. In addition, the output of the detector may be communicatively coupled to the controller 210.

In one example, the detector may be coupled to the controller 210 in any suitable manner (e.g., by one or more transmission media indicated by the dotted line shown in FIG. 1) such that the controller 210 may receive the output generated by the detector. By way of another example, if there are multiple detectors, the controller 210 may be coupled to the multiple detectors as described above. It is noted herein the controller 210 may be configured to detect one or more defects of the sample using detection data collected and transmitted by the detector, utilizing any method and/or algorithm known in the art to detect defects on the wafer. For example, the detector may be configured to accept instructions from another assembly of the system 200 including, but not limited to, controller 210.

It is noted herein that the detector may include any detector configured to collect and analyze illumination reflected, scattered, diffracted, and/or radiated from a surface of the sample to locate one or more defects. For purposes of the present disclosure, a defect may be classified as a void, short, particle, residue, scum, or any other defect known in the art.

It is noted herein the portion of the system 200 including the generation of monitoring data with the beam monitoring assembly 206 and the adjustment of the incident beam 203 to form the corrected beam 205 via the one or more motor drivers 220, where the adjustments to the incident beam 203 are based on one or more beam adjustments determined by the controller 210 from the monitoring data, is a closed compensation loop for purposes of the present disclosure. However, it is contemplated that one or more external sources may act on the system 200, such that the previously-described portion of the system 200 may instead be an open compensation loop. Therefore, the above description should not be interpreted as a limitation on the present disclosure but merely an illustration.

The embodiments of the system 200 illustrated in FIG. 2 may be further configured as described herein. In addition, the system 200 may be configured to perform any other steps(s) of any of the system and method embodiment(s) described herein.

FIGS. 3A-5 illustrate beam steering assemblies 204a, 204b, and 204c, in accordance with one or more embodiments of the present disclosure. It is noted herein the embodiments and examples described throughout the present disclosure should be interpreted to extend to the beam steering assemblies 204a, 204b, and 204c in FIGS. 3A-5 unless otherwise noted.

FIGS. 3A-3E illustrate the beam steering assembly 204a, in accordance with one or more embodiments of the present disclosure. In one embodiment, the beam steering assembly 204a includes a first prism 302 coupled to one or more motors 304. In another embodiment, the one or more motors 304 are coupled to one or more motor drivers 220. In another embodiment, the beam steering assembly 204a includes a second prism 306 coupled to one or more motors 308. In another embodiment, the one or more motors 308 are coupled to one or more motor drivers 220.

FIGS. 3B-3E illustrate how translating and/or tilting one or more of the prism 302 or the prism 306 adjusts the incident beam 203 to form the corrected beam 205. In one embodiment, changing the distance between the prism 302 and the prism 306 adjusts the translation component of a position of the incident beam 203 to form the corrected beam 205. In another embodiment, tilting one or more of the prism 302 and the prism 306 adjusts the pointing component of the position of the incident beam 203 to form the corrected beam 205. For example, FIG. 3E illustrates the tilting of both the prism 302 and the prism 306 through prism positions (a), (b), and (c). In another embodiment, a combination of changing the distance between the prism 302 and the prism 306, and tilting one or more of the prism 302 and the prism 306, adjusts the size of the incident beam 203 to form the corrected beam 205.

In another embodiment, linear motion of the prism 302 and/or the prism 306 is driven via one or more direct-drive motors 304 and/or 308, respectively. In another embodiment, rotational motion of the prism 302 and/or the prism 306 is driven via one or more stepper motors 304 and/or 308 operating in brushless mode, respectively. It is contemplated that the combination of one or more direct-drive motors for linear motion and one or more stepper motors operating in brushless mode for rotational motion is fast enough to actively adjust the incident beam 203 to form the corrected beam 205 via one or more of translation or rotation of one or more of the prisms 302 and 306.

Although embodiments of the present disclosure are directed to the beam steering assembly 204a having the two prisms 302 and 306, it is noted herein that the beam steering assembly 204a is not limited to the two prisms 302 and 306. For example, the beam steering assembly 204a may include may include up to an N number of prisms. For instance, the beam steering assembly 204a may include one or more pairs of prisms per beam adjustment direction (i.e. at least four prisms to adjust the incident beam 203 in both the x-direction and the y-direction to form the corrected beam 205, or at least two prisms to adjust the incident beam 203 in either the x-direction or the y-direction to form the corrected beam 205). Therefore, the above description should not be interpreted as a limitation on the present disclosure but merely an illustration.

Although a single motor driver 220 is illustrated in FIGS. 3A-3E as controlling the one or more motors 304 and the one or more motors 308, it is noted herein that at least some of the one or more motors 304 and the one or more motors 308 may be controlled by a motor-specific motor driver 220. Therefore, the above description should not be interpreted as a limitation on the present disclosure but merely an illustration.

FIG. 4 illustrates the beam steering assembly 204b, in accordance with one or more embodiments of the present disclosure. In one embodiment, the beam steering assembly 204b includes a reflecting mirror 402 coupled to one or more motors 404. For example, the one or more motors 404 may be a piezoelectric motor. In another embodiment, the one or more motors 404 are coupled to the motor driver 220. It is noted herein that where there are multiple motors 404, at least some of the multiple motors 404 may be controlled by a motor-specific motor driver 220.

In another embodiment, the reflecting mirror 402 at position (a) will reflect the incident beam 203 to the beam monitoring assembly 206 without adjusting the incident beam 203. In another embodiment, moving the reflecting mirror 402 from position (a) to position (b) adjusts the pointing component of the position of the incident beam 203 to form the corrected beam 205 in one or more of the x-direction and/or the y-direction. It is noted, however, that moving the reflecting mirror 402 from position (a) to position (b) will not adjust the translation component of the position of the incident beam 203 to form the corrected beam 205.

FIG. 5 illustrates the beam steering assembly 204c, in accordance with one or more embodiments of the present disclosure. In one embodiment, the beam steering assembly 204c includes a rectangular prism 502 coupled to one or more motors 504. For example, the one or more motors 404 may be a servo motor. In another embodiment, the one or more motors 404 are coupled to the motor driver 220. It is noted herein that where there are multiple motors 504, at least some of the multiple motors 504 may be controlled by a motor-specific motor driver 220.

In another embodiment, the prism 502 at position (a) will direct the incident beam 203 to the beam monitoring assembly 206 without adjusting the incident beam 203. In another embodiment, rotating the prism 502 from position (a) to position (b) adjusts the translation component of the position of the incident beam 203 to form the corrected beam 205 in one or more of the x-direction and/or the y-direction. It is noted, however, that rotating the prism 502 from position (a) to position (b) will not adjust the pointing component of the position of the incident beam 203 to form the corrected beam 205.

It is noted herein that beam steering assemblies 204a, 204b, and 204c are not limited to the previously-disclosed types of motors 304, 308, 404, or 504. For example, motors 304, 308, 404, or 504 may be any of a direct-drive motor, a direct drive motor, a stepper motor, a stepper motor operating in brushless mode, a piezoelectric motor, a servo motor, or any other motor known in the art. Therefore, the above description should not be interpreted as a limitation on the present disclosure but merely an illustration.

FIGS. 6A-6C illustrate beam monitoring assemblies 206a, 206b, and 206c, in accordance with one or more embodiments of the present disclosure. It is noted herein the embodiments and examples described throughout the present disclosure should be interpreted to extend to the beam monitoring assemblies 206a, 206b, and 206c in FIGS. 6A-6C unless otherwise noted.

In one embodiment, beam monitoring assemblies 206a, 206b, and 206c receive the corrected beam 205. In another embodiment, beam monitoring assemblies 206a, 206b, and 206c include a leak mirror 602. In another embodiment, the leak mirror 602 reflects at least a portion of the corrected beam 205 to the beam modulator 230. In another embodiment, the leak mirror 602 directs at least a portion of the corrected beam 205 to a beam splitter 604.

It is noted herein that the ratio of the corrected beam 205 reflected to the beam modulator 230 versus than the portion of the corrected beam 205 directed to the beam splitter 604 may be >99% :<1%. However, it is contemplated that the leak mirror 602 may reflect/direct the corrected beam 205 in any ratio. Therefore, the above description should not be interpreted as a limitation on the present disclosure but merely an illustration.

In another embodiment, the beam splitter 604 directs at least a portion of the corrected beam 205 directed by the leak mirror 602 to a first imaging device 610 through at least one optical element 606. For example, the at least one optical element 606 may include, but is not limited to, a telescope beam expander. For instance, the telescope beam expander 606 may increase the size, while maintaining beam collimation, of the splitter-directed portion of the corrected beam 205. By way of another example, the at least one optical element 606 may be any optical element known in the art.

In another embodiment, the beam splitter 604 reflects at least a portion of the corrected beam 205 directed by the leak mirror 602 to a second imaging device 612 through at least one optical element 608. For example, the at least one optical element 608 may include, but is not limited to, a focusing lens. For instance, the imaging device 612 will be on the focal plane of the focusing lens. By way of another example, the at least one optical element 608 may be any optical element known in the art.

It is noted herein that the ratio of the corrected beam 205 directed to the first imaging device 610 versus than the portion of the corrected beam 205 reflected to the second imaging device 612 may be 50/50. However, it is contemplated that the beam splitter 604 may reflect/direct the corrected beam 205 in any ratio. Therefore, the above description should not be interpreted as a limitation on the present disclosure but merely an illustration.

In one embodiment, as illustrated in FIG. 6A, imaging devices 610 and 612 are cameras capable of measuring one or more of illumination beam translational jitter, illumination beam pointing jitter, illumination beam size, and illumination beam breathing data in both the x-direction and the y-direction (i.e. are two-dimensional cameras). In another embodiment, the cameras 610 and 612 monitor one or more of translational jitter and pointing jitter of the corrected beam 205 as a function of time. For example, camera 610 may measure translational jitter, pointing jitter, and beam size in both the x-direction and the y-direction. By way of another example, camera 612 may measure the pointing jitter in both the x-direction and the y-direction. In another embodiment, the measurements taken by the cameras 610 and 612 may be processed via digital signal processor (DSP) code. For example, a centroid position fitting of an illumination beam measured by the cameras 610 and 612 may be determined via DSP code. In another embodiment, the decoupling of translational jitter and pointing jitter in the measurements taken by the cameras 610 and 612 may be done in real time via DSP code.

In one embodiment, as illustrated in FIG. 6B, imaging devices 620 and 622 are cameras capable of measuring one or more of illumination beam translational jitter, illumination beam pointing jitter, illumination beam size, and illumination beam breathing data in either the x-direction or the y-direction (i.e. are one-dimensional cameras). In another embodiment, the cameras 620 and 622 monitor one or more of translational jitter and pointing jitter of the corrected beam 205 as a function of time. For example, camera 620 may measure translational jitter, pointing jitter, and beam size in either the x-direction or the y-direction. By way of another example, camera 622 may measure the pointing jitter in either the x-direction or the y-direction. In another embodiment, the measurements taken by the cameras 620 and 622 may be processed via DSP code. For example, a centroid position fitting of the illumination beam measured by the cameras 620 and 622 may be determined via DSP code. By way of another example, the decoupling of translational jitter or pointing jitter in the illumination beam measurements taken by the cameras 620 and 622 may be done in real time via DSP code.

It is noted herein that utilizing the one-dimensional cameras 620 and 622 instead of the two-dimensional cameras 610 and 612 may result in a faster measurement performance at a lower data rate. It is further noted herein that where only pointing jitter is needed, the optical branches leading to cameras 612 or 622 in FIGS. 6A and 6B, respectively, may be removed.

In one embodiment, as illustrated in FIG. 6C, imaging devices 630 and 632 are bi-cell detectors capable of measuring illumination beam one or more of illumination beam translational jitter and illumination beam pointing jitter in either the x-direction or the y-direction. In another embodiment, the bi-cell detectors 630 and 632 monitor translational jitter or pointing jitter of the corrected beam 205 as a function of time. In another embodiment, bi-cell detector 630 measures a bi-cell signal A for a first half of a bi-cell, and bi-cell detector 632 measures a bi-cell signal B for a second half of the bi-cell. In another embodiment, a position of the illumination beam measured by the bi-cell detectors 630 and 632 is determined with Equation (1).

$$\text{Position} = \frac{A - B}{A + B} \quad \text{EQ. (1)}$$

In another embodiment, the cameras 630 and 632 measurements may be processed via DSP code. For example, the decoupling of translational jitter or pointing jitter in the illumination beam measured by the bi-cell detectors 630 and 632 measurements may be done in real time via DSP code.

Although embodiments of the present disclosure are directed to beam monitoring assemblies 206a, 206b, and 206c with two cameras or two bi-cell detectors, it is noted herein that the beam monitoring assemblies 206a, 206b, and 206c are not limited to two cameras or two bi-cell detectors. For example, the beam monitoring assemblies 206a, 206b, and 206c may include only one camera or bi-cell detector. By way of another example, the beam monitoring assemblies 206a, 206b, and 206c may include up to an N number of cameras or bi-cell detectors. By way of another example, the beam monitoring assemblies 206a, 206b, and 206c may include a mixed number of cameras and bi-cell detectors. Therefore, the above description should not be interpreted as a limitation on the present disclosure but merely an illustration.

Advantages of embodiments of the present disclosure include compensating for illumination beam misalignment in one or more of an x-direction and/or a y-direction. Advantages of embodiments of the present disclosure also include measuring one or more of the following: a translational component of the position of an illumination beam, a pointing component of the position of the illumination beam, an illumination beam size, and illumination beam breathing data. Advantages of embodiments of the present disclosure also include forming a corrected beam from the illumination beam by adjusting one or more of the following: the translational component of the position of the illumination beam, the pointing component of the position of the illumination beam, and drifts in the size of the illumination beam.

It is noted herein that the system 200 may be configured for a first set of capabilities which operate in both the x-direction and the y-direction. In one embodiment, the first set of capabilities includes measuring one or more of the following: a translational component of the position of an illumination beam, a pointing component of the position of the illumination beam, an illumination beam size, and illumination beam breathing data. In another embodiment, the first set of a corrected beam from the illumination beam by adjusting one or more of the following: the translational component of the position of the illumination beam, the pointing component of the position of the illumination beam, and drifts in the size of the illumination beam.

It is further noted herein that the system 200 may be configured with a second set of capabilities which operate in either an x-direction or a y-direction. In one embodiment, the second set of capabilities includes measuring one or more of the following: a translational component of the position of an illumination beam and/or a pointing component of the position of the illumination beam. In another embodiment, the second set of capabilities includes forming a corrected beam from the illumination beam by adjusting one or more of the following: the translational component of the position of the illumination beam and/or the pointing component of the position of the illumination beam.

It is further noted herein that the system 200 may be configured with at least a third set of capabilities which operate in one or more of an x-direction and/or a y-direction. In one embodiment, the at least a third set of capabilities includes one or more of the first set of capabilities and/or the second set of capabilities.

FIG. 7 illustrates a process flow diagram depicting a method 700 to compensate for illumination beam misalignment. The method may also include any other step(s) that can be performed by the output acquisition subsystem and/or computer subsystem(s) or system(s) described herein. The steps may be performed by one or more computer systems, which may be configured according to any of the embodiments described herein. It is noted herein that the steps of method 700 may be implemented all or in part by the system 200. It is recognized, however, that the method 700 is not limited to the system 200 in that additional or alternative system-level embodiments may carry out all or part of the steps of method 700.

In step 702, an incident beam 203 is adjusted to form a corrected beam 205. In one embodiment, the incident beam 203 is received by the beam steering assembly 204 from the illumination source 202. In another embodiment, the beam steering assembly 204 adjusts the incident beam 203 to form the corrected beam 205. For example, the system 200 may implement any of the beam steering assemblies 204*a*, 204*b*, or 204*c* to adjust the incident beam 203 to form the corrected beam 205. In another embodiment, the corrected beam 205 is directed by the beam steering assembly 204 to the beam monitoring assembly 206.

In step 704, monitoring data is generated. In one embodiment, the monitoring data is generated by the beam monitoring assembly 206. For example, the system 200 may implement any of the beam monitoring assemblies 206*a*, 206*b*, or 206*c* to generate the monitoring data. In another embodiment, the monitoring data includes one or more offset parameters of the corrected beam 205. In another embodiment, the one or more sets of monitoring data include one or more offset parameters of the corrected beam 205. For example, the one or more offset parameters may include, but are not limited to, an offset pointing component of the offset position of the corrected beam 205. By way of another example, the one or more offset parameters may include, but are not limited to, an offset translation component of the offset position of the corrected beam 205. By way of another example, the one or more offset parameters may include, but are not limited to, an offset beam size. By way of another example, the one or more offset parameters may include, but are not limited to, offset beam breathing data. In another embodiment, the one or more offset parameters of the corrected beam 205 include one or more of an x-direction component and/or a y-direction component. In another embodiment, the beam monitoring assembly 206 transmits the one or more sets of monitoring data for the corrected beam 205 to the controller 210.

In step 706, one or more zero parameters of the corrected beam 205 are stored. In one embodiment, the one or more zero parameters are stored by the controller 210. For example, the one or more zero parameters may include, but are not limited to, a zero pointing component of the zero position of the corrected beam 205. By way of another example, the zero parameters may include a zero translation component of the zero position of the corrected beam 205. By way of another example, the one or more zero parameters may include, but are not limited to, a zero beam size. By way of another example, the one or more zero parameters may include, but are not limited to, zero beam breathing data. In another embodiment, the one or more zero parameters of the corrected beam 205 include one or more of an x-direction component and/or a y-direction component.

In step 708, one or more differences between the one or more zero parameters and the one or more offset parameters of the corrected beam 205 are calculated. In one embodiment, the one or more offset parameters are received by the controller 210 from the beam monitoring assembly 206. In another embodiment, the controller 210 calculates one or more differences between the one or more zero parameters and the one or more offset parameters of the corrected beam 205. For example, calculating the one or more differences may include calculating a pointing difference between the zero pointing component of the zero position of the corrected beam 205 and the offset pointing component of the offset position of the corrected beam 205. By way of another example, calculating one or more differences may include calculating a translation difference between the zero translation component of the zero position of the corrected beam 205 and the offset translation component of the offset position of the corrected beam 205. By way of another example, calculating one or more differences may include calculating a beam size difference between the zero beam size and the offset beam size. By way of another example, calculating one or more differences may include calculating a beam breathing data difference between the zero beam breathing data and the offset beam breathing data.

In step 710, one or more beam position adjustments of the incident beam 203 are determined. In one embodiment, the one or more beam position adjustments of the incident beam 203 are determined by the controller 210. In another embodiment, the one or more beam adjustments are based on the calculated one or more differences between the one or more zero parameters and the one or more offset parameters of the corrected beam 205. In another embodiment, the one or more beam position adjustments are transmitted by the controller 210 to the one or more motor drivers 220.

In step 712, a beam steering assembly is directed to adjust the incident beam 203 to form the corrected beam 205. In one embodiment, the beam steering assembly 204 includes one or more motors coupled to one or more optical components. For example, the one or more motors are actuated by the one or more motor drivers 220. In another embodiment, the one or more beam positions adjustments are received by the one or more motor drivers 220. For example, the one or more beam adjustments may include one or more commands to actuate the one or more motors of the beam steering assembly 204. For instance, actuating the one or more motors moves the one or more optical components, which adjusts the incident beam 203 to form the corrected beam 205.

In an additional step, encoder data for the one or more motors following actuation of the one or more motors is generated. In one embodiment, the beam steering assembly 204 includes one or more encoders. In another embodiment, the actuation of the one or more motors via the one or more motor drivers 220 based on the one or more beam position adjustments is recorded by the one or more encoders as the encoder data. In another embodiment, the encoder data is transmitted to the controller 210.

In an additional step, the actuation of the one or more motors is verified based on the encoder data. In one embodiment, the controller 210 receives the encoder data. In another embodiment, the controller 210 compares the actuation of the one or more motors recorded in the encoder data to the one or more beam position adjustments transmitted to the one or more motor drivers 220.

All of the methods described herein may include storing results of one or more steps of the method embodiments in a memory medium. The results may include any of the results described herein and may be stored in any manner known in the art. The memory medium may include any memory medium described herein or any other suitable memory medium known in the art. After the results have been stored, the results can be accessed in the memory medium and used by any of the method or system embodiments described herein, formatted for display to a user, used by another software module, method, or system, etc. Furthermore, the results may be stored "permanently," "semi-permanently," temporarily, or for some period of time. For example, the memory medium may be random access memory (RAM), and the results may not necessarily persist indefinitely in the memory medium.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B".

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Accordingly, the scope of the invention should be limited only by the claims appended hereto.

What is claimed:

1. A system comprising:
a beam steering assembly configured to adjust an incident beam to form a corrected beam;
a beam monitoring assembly optically coupled to the beam steering assembly, the beam monitoring assembly configured to generate monitoring data for the corrected beam, wherein the monitoring data includes one or more offset parameters of the corrected beam, wherein the beam monitoring assembly comprises:
a leak mirror configured to:
receive the corrected beam from the beam steering assembly;
reflect a first portion of the corrected beam; and
transmit a second portion of the corrected beam; and
a beam splitter configured to:
receive the second portion of the corrected beam transmitted by the leak mirror;
transmit a third portion of the corrected beam through at least a first optical element to a first imaging device; and
reflect a fourth portion of the corrected beam through at least a second optical element to a second imaging device,
wherein the third portion of the corrected beam and the fourth portion of the corrected beam are formed from the second portion of the corrected beam; and
a controller communicatively coupled to the beam monitoring assembly and the beam steering assembly, wherein the controller includes one or more processors configured to execute a set of program instructions stored in memory, wherein the program instructions are configured to cause the one or more processors to:
store one or more zero parameters of the corrected beam;
calculate at least one difference between the one or more zero parameters and the one or more offset parameters of the corrected beam;
determine one or more beam position adjustments of the incident beam based on the at least one difference between the one or more zero parameters and the one or more offset parameters of the corrected beam; and
direct the beam steering assembly, via one or more motor drivers, to actuate one or more motors to adjust the incident beam to form the corrected beam.

2. The system in claim 1, wherein the one or more offset parameters of the corrected beam includes at least one of:
an offset pointing component of an offset position of the corrected beam, an offset translation component of the offset position of the corrected beam, an offset beam size, or offset beam breathing data.

3. The system in claim 2, wherein at least one of the offset pointing component of the offset position of the corrected beam, the offset translation component of the offset position of the corrected beam, the offset beam size, or the offset beam breathing data includes at least one of an x-direction component or a y-direction component.

4. The system in claim 1, wherein the one or more zero parameters of the corrected beam includes at least one of:
a zero pointing component of a zero position of the corrected beam, a zero translation component of the zero position of the corrected beam, a zero beam size, or zero beam breathing data.

5. The system in claim 4, wherein at least one of the zero pointing component of the zero position of the corrected beam, the zero translation component of the zero position of the corrected beam, the zero beam size, or the zero beam breathing data includes at least one of an x-direction component or a y-direction component.

6. The system in claim 1, wherein calculating the difference between the one or more zero parameters and the one or more offset parameters of the corrected beam includes calculating a pointing difference between a zero pointing component of a zero position of the corrected beam and an offset pointing component of an offset position of the corrected beam.

7. The system in claim 1, wherein calculating the difference between the one or more zero parameters and the one or more offset parameters of the corrected beam includes calculating a translation difference between a zero translation component of a zero position of the corrected beam and an offset translation component of an offset position of the corrected beam.

8. The system in claim 1, wherein calculating the difference between the one or more zero parameters and the one or more offset parameters of the corrected beam includes calculating a beam size difference between a zero beam size and an offset beam size.

9. The system in claim 1, wherein calculating the difference between the one or more zero parameters and the one or more offset parameters of the corrected beam includes calculating a beam breathing data difference between zero beam breathing data and offset beam breathing data.

10. The system in claim 1, wherein the beam steering assembly is further configured to:
generate encoder data for the one or more motors following actuation of the one or more motors.

11. The system in claim 10, wherein the program instructions are further configured to:
verify the actuation of the one or more motors in response to the one or more beam position adjustments via the encoder data.

12. The system in claim 1, wherein the beam steering assembly comprises:
at least two prisms coupled to the one or more motors,
wherein actuating the one or more motors to alter a distance between the two prisms via the one or more motors adjusts a translation component of a position of the incident beam to form the corrected beam,
wherein actuating the one or more motors to tilt at least one of the two prisms via the one or more motors adjusts a pointing component of the position of the incident beam to form the corrected beam,
wherein actuating the one or more motors to simultaneously alter the distance between the two prisms and tilt at least one of the two prisms via the one or more motors adjusts a beam size of the incident beam to form the corrected beam.

13. The system in claim 1, wherein the beam steering assembly comprises:
a reflecting mirror coupled to the one or more motors,
wherein displacing the reflecting mirror via the one or more motors adjusts a pointing component of a position of the incident beam to form the corrected beam.

14. The system in claim 1, wherein the beam steering assembly comprises:
at least one prism coupled to the one or more motors,
wherein rotating the prism via the one or more motors adjusts a translation component of a position of the incident beam to form the corrected beam.

15. The system in claim 1, wherein the first optical element is a telescope beam expander, wherein the second optical element is a focusing lens.

16. The system in claim 15, wherein the first imaging device and the second imaging device is a camera, wherein each camera is capable of measuring the corrected beam in at least one of an x-direction or a y-direction.

17. The system in claim 16, wherein the camera of the first imaging device measures at least a translation component of a position of the corrected beam and a pointing component of the position of the corrected beam, wherein the camera of the second imaging device measures the pointing component of the position of the corrected beam.

18. The system in claim 15, wherein at least one of the first imaging device and the second imaging device is a bi-cell detector, wherein each bi-cell detector is capable of measuring the corrected beam in either an x-direction or a y-direction.

19. The system in claim 18, wherein the bi-cell detector of the first imaging device measures at least a translation component of a position of the corrected beam and a pointing component of the position of the corrected beam, wherein the bi-cell detector of the second imaging device measures the pointing component of the position of the corrected beam.

20. The system in claim 15, further comprising:
a beam modulator, wherein the beam modulator receives the first portion of the corrected beam reflected by the leak mirror.

21. The system in claim 1, wherein the one or more motors includes at least one of:
a direct drive motor, a stepper motor, a brushless motor, a piezoelectric motor, or a servo motor.

22. The system in claim 1, further comprising:
at least one illumination source configured to generate the incident beam.

23. A method, comprising:
receiving an incident beam;
adjusting the incident beam to form a corrected beam via a beam steering assembly;
generating monitoring data for the corrected beam via a beam monitoring assembly optically coupled to the beam steering assembly, wherein the monitoring data includes one or more offset parameters of the corrected beam, wherein the beam monitoring assembly comprises:
a leak mirror configured to:
receive the corrected beam from the beam steering assembly;
reflect a first portion of the corrected beam; and
transmit a second portion of the corrected beam; and
a beam splitter configured to:
receive the second portion of the corrected beam transmitted by the leak mirror;
transmit a third portion of the corrected beam through at least a first optical element to a first imaging device; and
reflect a fourth portion of the corrected beam through at least a second optical element to a second imaging device,
wherein the third portion of the corrected beam and the fourth portion of the corrected beam are formed from the second portion of the corrected beam;
storing one or more zero parameters of the corrected beam;
calculating at least one difference between the one or more zero parameters and the one or more offset parameters of the corrected beam;
determining one or more beam position adjustments of the incident beam based on the at least one difference between the one or more zero parameters and the one or more offset parameters of the corrected beam; and
directing the beam steering assembly, via one or more motor drivers, to actuate one or more motors based on the one or more beam position adjustments to adjust the incident beam to form the corrected beam.

24. The method of claim 23, wherein the one or more offset parameters of the corrected beam includes at least one of:
an offset pointing component of an offset position of the corrected beam, an offset translation component of the offset position of the corrected beam, an offset beam size, or offset beam breathing data.

25. The method of claim 24, wherein at least one of the offset pointing component of the offset position of the corrected beam, the offset translation component of the offset position of the corrected beam, the offset beam size, or the offset beam breathing data includes at least one of an x-direction component or a y-direction component.

26. The method of claim 23, wherein the one or more zero parameters of the corrected beam includes at least one of:
a zero pointing component of a zero position of the corrected beam, a zero translation component of the zero position of the corrected beam, a zero beam size, or zero beam breathing data.

27. The method of claim 26, wherein at least one of the zero pointing component of the zero position of the corrected beam, the zero translation component of the zero position of the corrected beam, the zero beam size, or the zero beam breathing data includes at least one of an x-direction component or a y-direction component.

28. The method of claim 23, wherein calculating the difference between the one or more zero parameters and the one or more offset parameters of the corrected beam includes calculating a pointing difference between a zero pointing component of a zero position of the corrected beam and an offset pointing component of an offset position of the corrected beam.

29. The method of claim 23, wherein calculating the difference between the one or more zero parameters and the one or more offset parameters of the corrected beam includes calculating a translation difference between a zero translation component of a zero position of the corrected beam and an offset translation component of an offset position of the corrected beam.

30. The method of claim 23, wherein calculating the difference between the one or more zero parameters and the one or more offset parameters of the corrected beam includes calculating a beam size difference between a zero beam size and an offset beam size.

31. The method of claim 23, wherein calculating the difference between the one or more zero parameters and the one or more offset parameters of the corrected beam includes calculating a beam breathing data difference between zero beam breathing data and offset beam breathing data.

32. The method of claim 23, further comprising:
generating encoder data for the one or more motors following actuation of the one or more motors.

33. The method of claim 32, further comprising:
verifying the actuation of the one or more motors based on the encoder data.

34. The method of claim 23, wherein the beam steering assembly comprises:
at least two prisms coupled to the one or more motors,
wherein actuating the one or more motors to alter a distance between the two prisms via the one or more motors adjusts a translation component of a position of the incident beam to form the corrected beam,
wherein actuating the one or more motors to tilt at least one of the two prisms via the one or more motors adjusts a pointing component of the position of the incident beam to form the corrected beam,
wherein actuating the one or more motors to simultaneously alter the distance between the two prisms and tilt at least one of the two prisms via the one or more motors adjusts a beam size of the incident beam to form the corrected beam.

35. The method of claim 23, wherein the beam steering assembly comprises:
a reflecting mirror coupled to the one or more motors,
wherein displacing the reflecting mirror via the one or more motors adjusts a pointing component of a position of the incident beam to form the corrected beam.

36. The method of claim 23, wherein the beam steering assembly comprises:
at least one prism coupled to the one or more motors,
wherein rotating the prism via the one or more motors adjusts a translation component of a position of the incident beam to form the corrected beam.

37. The method of claim 23, wherein the first optical element is a telescope beam expander, wherein the second optical element is a focusing lens.

38. The method of claim 37, wherein the first imaging device and the second imaging device is a camera, wherein each camera is capable of measuring the corrected beam in at least one of an x-direction or a y-direction.

39. The method of claim 38, wherein the camera of the first imaging device measures at least a translation component of a position of the corrected beam and a pointing component of the position of the corrected beam, wherein the camera of the second imaging device measures the pointing component of the position of the corrected beam.

40. The method of claim 37, wherein at least one of the first imaging device and the second imaging device is a bi-cell detector, wherein each bi-cell detector is capable of measuring the corrected beam in either an x-direction or a y-direction.

41. The method of claim 40, wherein the bi-cell detector of the first imaging device measures at least a translation component of a position of the corrected beam and a pointing component of the position of the corrected beam, wherein the bi-cell detector of the second imaging device measures the pointing component of the position of the corrected beam.

42. The method of claim 37, wherein the beam monitoring assembly further comprises:
a beam modulator, where the beam modulator is configured to receive the first portion of the corrected beam reflected by the leak mirror.

43. The method of claim 23, wherein the one or more motors includes at least one of:
a direct drive motor, a stepper motor, a brushless motor, a piezoelectric motor, or a servo motor.

44. The method of claim 23, wherein the incident beam is received from an illumination source configured to generate the incident beam.

* * * * *